(12) United States Patent
Flockerzi et al.

(10) Patent No.: US 8,324,404 B2
(45) Date of Patent: Dec. 4, 2012

(54) 3-THIA-10-AZA-PHENANTHRENE DERIVATIVES

(75) Inventors: Dieter Flockerzi, Allensbach (DE); Jens Christoffers, Oldenburg (DE); Anna Christoffers, Oldenburg (DE)

(73) Assignee: Nycomed GmbH, Constance (DE)

( * ) Notice: Subject to any disclaimer, the term of this patent is extended or adjusted under 35 U.S.C. 154(b) by 413 days.

(21) Appl. No.: 12/453,966

(22) Filed: May 28, 2009

(65) Prior Publication Data

US 2009/0239895 A1 Sep. 24, 2009

Related U.S. Application Data

(62) Division of application No. 11/661,377, filed as application No. PCT/EP2005/054365 on Sep. 5, 2005, now Pat. No. 7,589,205.

(30) Foreign Application Priority Data

Sep. 8, 2004 (EP) ..................... 04104319

(51) Int. Cl.
*C07D 335/02* (2006.01)

(52) U.S. Cl. .......................................... 549/28
(58) Field of Classification Search ...................... 549/28
See application file for complete search history.

(56) References Cited

U.S. PATENT DOCUMENTS

| | | | |
|---|---|---|---|
| 6,008,215 A | 12/1999 | Flockerzi | |
| 6,143,759 A | 11/2000 | Flockerzi | |
| 6,191,138 B1 * | 2/2001 | Gutterer | 514/287 |
| 6,306,869 B1 | 10/2001 | Flockerzi | |
| 6,436,952 B1 | 8/2002 | Flockerzi | |
| 6,525,055 B1 | 2/2003 | Napoletano et al. | |
| 6,534,518 B1 | 3/2003 | Gutterer | |

FOREIGN PATENT DOCUMENTS

| | | |
|---|---|---|
| WO | WO 97/28131 | 8/1997 |
| WO | WO 98/21208 | 5/1998 |
| WO | WO 98/40382 | 9/1998 |
| WO | WO 99/57118 | 11/1999 |
| WO | WO 00/12501 | 3/2000 |
| WO | 00/42017 A1 | 7/2000 |
| WO | 00/42020 A1 | 7/2000 |
| WO | WO 00/42018 | 7/2000 |
| WO | 00/56727 A1 | 9/2000 |
| WO | 00/56728 A1 | 9/2000 |
| WO | WO 02/056160 | 1/2002 |
| WO | WO 2004/019944 | 3/2004 |
| WO | WO 2005/087745 | 9/2005 |
| WO | WO 2006/027344 | 3/2006 |

OTHER PUBLICATIONS

Denmark, Scott E. et al., "Catalytic Epoxidation of Alkenes with Oxone", J. Org. Chem., 1995, pp. 1391-1407, vol. 60, No. 5, American Chemical Society.

Garst, Michael E. et al., "Epoxyannulation. 4. Reactions of 1,5-, 1,6-, and 1,7-Oxosulfonium Salts", J. Org. Chem., 1983, pp. 8-16, vol. 48, No. 1, American Chemical Society.

Johnson, Peter Y. et al., "Photochemical Reactions of γ-Keto Sulfides", The Journal of Organic Chemistry, Mar. 1970, pp. 584-592, vol. 35, No. 3.

McGill, John M. et al., "Hydride Reagents for Stereoselective Reductive Amination. An Improved Preparation of 3-Endo-Tropanamine", Tetrahedron Letters, 1996, pp. 3977-3980, vol. 37, No. 23, Elsevier Science Ltd., Great Britain.

Russell, Michael G.N. et al., "3-[3-(Piperidin-1-yl)propyl]indoles as Highly Selective h5-$HT_{1D}$ Receptor Agonists", J. Med. Chem., 1999, pp. 4981-5001, vol. 42, No. 24, American Chemical Society.

Dorwald, F.A., "Side Reactions in Organic Synthesis", 2005, Wiley: VCH, Weinheim, p. IX of Preface.

Dronov, V.I., et al., "The Thioalkylation Reaction, VIII. Synthesis of Cyclic γ-ketosulphides", J Org Chem, (1985), vol. 21, No. 5, pp. 1102-1107. With Full English Translation.

* cited by examiner

*Primary Examiner* — Robert Havlin
(74) *Attorney, Agent, or Firm* — Nath, Goldberg & Meyer; Sheldon M. McGee

(57) ABSTRACT

The compounds of formula I

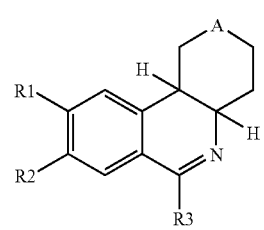

(1)

in which A, R1, R2 and R3 have the meanings as given in the description, are novel effective PDE4 inhibitors.

7 Claims, No Drawings

3-THIA-10-AZA-PHENANTHRENE DERIVATIVES

This application is a divisional application of U.S. Ser. No. 11/661,377 which was filed on Mar. 26, 2007 under 35 U.S.C. 371 as a national stage of PCT/EP2005/054365, filed Sep. 5, 2005, and claims the benefit of EP 04104319.1, filed Sep. 8, 2004.

FIELD OF APPLICATION OF THE INVENTION

The invention relates to novel 3-thia-10-aza-phenanthrene derivatives, which are used in the pharmaceutical industry for the production of pharmaceutical compositions. The invention also relates to intermediate compounds, novel 3-(3,4-dialkoxy-phenyl)-tetrahydro-thiopyran-4-one and 3-(3,4-dialkoxyphenyl)-1,1-dioxo-hexahydro-1l$^6$-thiopyran-4-ylamine derivatives, which are useful for the preparation of the 3-thia-10-aza-phenanthrene derivatives and processes for producing said intermediate compounds.

KNOWN TECHNICAL BACKGROUND

The international applications WO98/21208 (=U.S. Pat. No. 6,008,215), WO98/40382 (=U.S. Pat. No. 6,143,759), WO99/57118 (=U.S. Pat. No. 6,306,869) and WO00/12501 describe 6-phenylbenzonaphthyridines and their N-oxides as PDE3/4 inhibitors. In the International patent application WO02/05616 6-phenylphenanthridines are described as PDE4 inhibitors.

DESCRIPTION OF THE INVENTION

It has now been found that the compounds of formula 1, which are described in more detail below and which differ from the prior-art compounds in particular by substitution of a N—R group by a S(O)$_2$ group, have surprising and particularly advantageous properties.

The invention thus relates in a first aspect to compounds of formula 1,

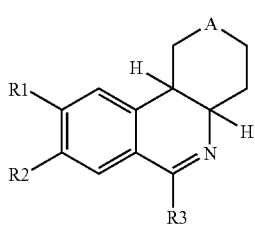

(1)

in which
A is S, S(O) or S(O)$_2$,
R1 is 1-4C-alkoxy, 3-7C-cycloalkoxy, 3-7C-cycloalkylmethoxy or 1-4C-alkoxy which is completely or predominantly substituted by fluorine,
R2 is 1-4C-alkoxy, 3-7C-cycloalkoxy, 3-7C-cycloalkylmethoxy or 1-4C-alkoxy which is completely or predominantly substituted by fluorine,
or in which
R1 and R2 together are a 1-2C-alkylenedioxy group,
R3 is a phenyl radical which is substituted by R4 and R5, wherein
R4 is hydrogen, hydroxyl, halogen, nitro, 1-4C-alkyl, trifluoromethyl or 1-4C-alkoxy,
R5 is CO—R6 or CO—R7, wherein
R6 is hydroxyl, 1-8C-alkoxy, 3-7C-cycloalkoxy or 3-7C-cycloalkylmethoxy and
R7 is N(R71)R72, wherein R71 and R72 independently of one another are hydrogen, 1-7C-alkyl, 3-7C-cycloalkyl or 3-7C-cycloalkylmethyl, or wherein R71 and R72, together and including the nitrogen atom to which both are bonded, are a 1-pyrrolidinyl, 1-piperidyl, 1-hexahydroazepinyl or 4-morpholinyl radical,
or a hydrate, solvate or salt thereof, or a hydrate or solvate of a salt thereof, or a N-oxide thereof, or a salt, hydrate or solvate of the latter.

1-4C-Alkyl represents a straight-chain or branched alkyl radical having 1 to 4 carbon atoms. Examples which may be mentioned are the butyl, isobutyl, sec-butyl, tert-butyl, propyl, isopropyl and, preferably, the ethyl and methyl radicals.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and, preferably, the ethoxy and methoxy radicals.

3-7C-Cycloalkoxy represents cyclopropyloxy, cyclobutyloxy, cyclopentyloxy, cyclohexyloxy and cycloheptyloxy, of which cyclopropyloxy, cyclobutyloxy and cyclopentyloxy are preferred.

3-7C-Cycloalkylmethoxy represents cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

As 1-4C-Alkoxy which is completely or predominantly substituted by fluorine, the 2,2,3,3,3-pentafluoropropoxy, the perfluoroethoxy, the 1,1,2,2-tetrafluoroethoxy, the 1,2,2-trifluoroethoxy, the trifluoromethoxy, in particular the 2,2,2-trifluoroethoxy, and preferably the difluoromethoxy radicals, for example, may be mentioned. "Predominantly" in this connection means that more than half of the hydrogen atoms of the 1-4C-alkoxy group are replaced by fluorine atoms.

1-2C-Alkylenedioxy represents, for example, the methylenedioxy [—O—CH$_2$—O-] or the ethylenedioxy radical [—O—CH$_2$CH$_2$—O–].

Halogen within the meaning of the invention is fluorine, chlorine or bromine.

1-8C-Alkoxy represents radicals, which, in addition to the oxygen atom, contain a straight-chain or branched alkyl radical having 1 to 8 carbon atoms. Examples which may be mentioned are the octyloxy, heptyloxy, hexyloxy, pentyloxy, methylbutoxy, ethylpropoxy, butoxy, isobutoxy, sec-butoxy, tert-butoxy, propoxy or, preferably, the isopropoxy, ethoxy or methoxy radical.

1-7C-Alkyl represents straight-chain or branched alkyl radicals having 1 to 7 carbon atoms. Examples which may be mentioned are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tertbutyl, propyl, isopropyl, ethyl or methyl radical.

3-7C-Cycloalkyl represents the cyclopropyl, cyclobutyl, cyclopentyl, cyclohexyl or cycloheptyl radical.

3-7C-Cycloalkylmethyl represents a methyl radical which is substituted by one of the abovementioned 3-7C-cycloalkyl radicals. Examples which may be mentioned are the cycloalkylmethyl radicals cyclopropylmethyl, cyclobutylmethyl and cyclopentylmethyl.

The substituents R4 and R5 can be attached to the phenyl radical R3 in any position. Preferred are those cases, in which R4 and R5 are attached in the para- and/or meta-position. Most preferred are those cases, in which R4 has the meaning hydrogen and R5 is attached in the meta- or para-position.

Salts of the compounds according to the present invention include all acid addition salts and all salts with bases, specifically all pharmaceutically acceptable inorganic and organic acid addition salts and all pharmaceutically acceptable salts with bases, more specifically all pharmaceutically acceptable inorganic and organic acid addition salts and all pharmaceutically acceptable salts with bases customarily used in pharmacy.

Acid addition salts include, but are not limited to, hydrochlorides, hydrobromides, phosphates, nitrates, sulfates, acetates, citrates, D-gluconates, benzoates, 2-(4-hydroxybenzoyl)benzoates, butyrates, sulfosalicylates, maleates, laurates, malates, fumarates, succinates, oxalates, tartrates, stearates, toluenesulfonates, methanesulfonates, 3-hydroxy-2-naphthoates and trifluoroacetates. Of these, hydrochlorides, tartrates, maleates and fumarates are preferred.

Examples of salts with bases include, but are not limited to, lithium, sodium, potassium, calcium, aluminum, magnesium, titanium, ammonium, meglumine and guanidinium salts.

The salts include water-insoluble and, particularly, water-soluble salts.

An embodiment (embodiment A) of the present invention include those compounds of formula 1, in which
A is S or S(O),
R1 is 1-2C-alkoxy or 1-2C-alkoxy which is completely or predominantly substituted by fluorine,
R2 is 1-2C-alkoxy or 1-2C-alkoxy which is completely or predominantly substituted by fluorine,
R3 is a phenyl radical which is substituted by R4 and R5, wherein
R4 is hydrogen,
R5 is CO—R6 or CO—R7, wherein
R6 is hydroxyl, 1-8C-alkoxy, 3-7C-cycloalkoxy or 3-7C-cycloalkylmethoxy and
R7 is N(R71)R72, wherein R71 and R72 independently of one another are hydrogen, 1-7C-alkyl, 3-7C-cycloalkyl or 3-7C-cycloalkylmethyl, or wherein R71 and R72, together and including the nitrogen atom to which both are bonded, are a 1-pyrrolidinyl, 1-piperidyl, 1-hexahydroazepinyl or 4-morpholinyl radical,
or a hydrate, solvate or salt thereof, or a hydrate or solvate of a salt thereof.

Compounds of formula 1 of embodiment A to be emphasized are those in which
A is S or S(O),
R1 is methoxy or ethoxy,
R2 is methoxy or ethoxy,
R3 is a phenyl radical which is substituted by R4 and R5, wherein
R4 is hydrogen,
R5 is CO—R6 or CO—R7, wherein
R6 is hydroxyl or 1-4C-alkoxy and
R7 is N(R71)R72, wherein R71 and R72 independently of one another are hydrogen or 1-4C-alkyl, or wherein R71 and R72, together and including the nitrogen atom to which both are bonded, are a 1-piperidyl, 1-hexahydroazepinyl or 4-morpholinyl radical,
or a hydrate, solvate or salt thereof, or a hydrate or solvate of a salt thereof.

Preferred compounds of formula 1 of embodiment A are those in which
A is S or S(O),
R1 is methoxy or ethoxy,
R2 is methoxy or ethoxy,
R3 is a phenyl radical which is substituted by R4 and R5, wherein
R4 is hydrogen,
R5 is CO—R6 or CO—R7, wherein
R6 is 1-2C-alkoxy and
R7 is N(R71)R72, wherein R71 and R72 independently of one another are 1-4C-alkyl, or a hydrate, solvate or salt thereof, or a hydrate or solvate of a salt thereof.

Particularly preferred compounds of formula 1 of embodiment A are those in which
A is S or S(O),
R1 is methoxy or ethoxy,
R2 is methoxy or ethoxy,
R3 is a phenyl radical which is substituted by R4 and R5, wherein
R4 is hydrogen,
R5 is CO—R7, wherein
R7 is N(R71)R72, wherein R71 and R72 are isopropyl,
or a hydrate, solvate or salt thereof, or a hydrate or solvate of a salt thereof.

Another embodiment (embodiment B) of the present invention include those compounds of formula 1 in which
A is $S(O)_2$,
R1 is 1-4C-alkoxy, 3-7C-cycloalkoxy, 3-7C-cycloalkylmethoxy or 1-4C-alkoxy which is completely or predominantly substituted by fluorine,
R2 is 1-4C-alkoxy, 3-7C-cycloalkoxy, 3-7C-cycloalkylmethoxy or 1-4C-alkoxy which is completely or predominantly substituted by fluorine,
or in which
R1 and R2 together are a 1-2C-alkylenedioxy group,
R3 is a phenyl radical which is substituted by R4 and R5, where
R4 is hydrogen, hydroxyl, halogen, nitro, 1-4C-alkyl, trifluoromethyl or 1-4C-alkoxy,
R5 is CO—R6 or CO—R7, where
R6 is hydroxyl, 1-8C-alkoxy, 3-7C-cycloalkoxy or 3-7C-cycloalkylmethoxy and
R7 is N(R71)R72, where R71 and R72 independently of one another are hydrogen, 1-7C-alkyl, 3-7C-cycloalkyl or 3-7C-cycloalkylmethyl, or where R71 and R72, together and including the nitrogen atom to which both are bonded, are a 1-pyrrolidinyl, 1-piperidyl, 1-hexahydroazepinyl or 4-morpholinyl radical,
or a hydrate, solvate or salt thereof, or a hydrate or solvate of a salt thereof, or a N-oxide thereof, or a salt, hydrate or solvate of the latter.

Compounds of formula 1 of embodiment B to be emphasized are those in which
A is $S(O)_2$,
R1 is 1-2C-alkoxy or 1-2C-alkoxy which is completely or predominantly substituted by fluorine,
R2 is 1-2C-alkoxy or 1-2C-alkoxy which is completely or predominantly substituted by fluorine,
R3 is a phenyl radical which is substituted by R4 and R5, where R4 is hydrogen,
R5 is CO—R6 or CO—R7, where
R6 is hydroxyl, 1-8C-alkoxy, 3-7C-cycloalkoxy or 3-7C-cycloalkylmethoxy and
R7 is N(R71)R72, where R71 and R72 independently of one another are hydrogen, 1-7C-alkyl, 3-7C-cycloalkyl or 3-7C-cycloalkylmethyl, or where R71 and R72, together and including the nitrogen atom to which both are bonded, are a 1-pyrrolidinyl, 1-piperidyl, 1-hexahydroazepinyl or 4-morpholinyl radical, or a hydrate, solvate or salt thereof, or a hydrate or solvate of a salt thereof, or a N-oxide thereof, or a salt, hydrate or solvate of the latter.

Compounds of formula 1 of embodiment B to be particularly emphasized are those in which
A is $S(O)_2$,
R1 is methoxy or ethoxy,
R2 is methoxy or ethoxy,
R3 is a phenyl radical which is substituted by R4 and R5, where
R4 is hydrogen,
R5 is CO—R6 or CO—R7, where
R6 is hydroxyl or 1-4C-alkoxy and
R7 is N(R71)R72, where R71 and R72 independently of one another are hydrogen or 1-4C-alkyl, or where R71 and R72, together and including the nitrogen atom to which both are bonded, are a 1-piperidyl, 1-hexahydroazepinyl or 4-morpholinyl radical,
or a hydrate, solvate or salt thereof, or a hydrate or solvate of a salt thereof, or a N-oxide thereof, or a salt, hydrate or solvate of the latter.

Preferred compounds of formula 1 of embodiment B are those in which
A is $S(O)_2$,
R1 is methoxy or ethoxy,
R2 is methoxy or ethoxy,
R3 is a phenyl radical which is substituted by R4 and R5, where
R4 is hydrogen,
R5 is CO—R6 or CO—R7, where
R6 is 1-2C-alkoxy and
R7 is N(R71)R72, where R71 and R72 independently of one another are 1-4C-alkyl,
or a hydrate, solvate or salt thereof, or a hydrate or solvate of a salt thereof, or a N-oxide thereof, or a salt, hydrate or solvate of the latter.

Particularly preferred compounds of formula 1 of embodiment B are those in which
A is $S(O)_2$,
R1 is methoxy or ethoxy,
R2 is methoxy or ethoxy,
R3 is a phenyl radical which is substituted by R4 and R5, where
R4 is hydrogen,
R5 is CO—R7, where
R7 is N(R71)R72, where R71 and R72 are isopropyl,
or a hydrate, solvate or salt thereof, or a hydrate or solvate of a salt thereof.

A special embodiment of the present invention includes those compounds of formula 1, or a hydrate, solvate or salt thereof, or a hydrate or solvate of a salt thereof in which R1 is ethoxy and R2 is methoxy.

A further special embodiment of the present invention includes those compounds of formula 1, or a hydrate, solvate or salt thereof, or a hydrate or solvate of a salt thereof, in which R1 is ethoxy, R2 is methoxy and A represents S.

Still a further embodiment of the present invention includes those compounds of formula 1, or a hydrate, solvate or salt thereof, or a hydrate or solvate of a salt thereof, in which R1 is ethoxy, R2 is methoxy and A represents S(O).

Another special embodiment of the present invention includes those compounds of formula 1, or a hydrate, solvate or salt thereof, or a hydrate or solvate of a salt thereof, in which R1 is ethoxy, R2 is methoxy and A represents $S(O)_2$.

Still another special embodiment of the present invention includes those compounds of formula 1, or a hydrate, solvate or salt thereof, or a hydrate or solvate of a salt thereof, in which R1 is ethoxy, R2 is methoxy, A represents S, S(O) or $S(O)_2$, preferably S or S(O), in particular S, and R3 is a phenyl radical substituted in para position by diisopropylaminocarbonyl.

The compounds of the present invention and their hydrates, solvates, salts and N-oxides include chiral compounds. Each of the chiral centers present in said compounds, hydrates, solvates, salts and N-oxides may have the absolute configuration R or the absolute configuration S (according to the rules of Cahn, Ingold and Prelog).

In particular, the compounds of formula 1 include chiral compounds having chiral centers at least in positions 4a and 10a Numbering:

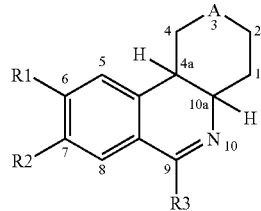

(1)

Accordingly, the present invention includes all conceivable pure diastereomers and pure enantiomers of the compounds, hydrates, solvates, salts and N-oxides according to the present invention, and all mixtures thereof in any mixing ratio, including the racemates.

The expression "pure enantiomere" according to the present invention means that the concerned enantiomere has an enantiomeric purity of 90% minimum enantiomeric excess (ee), preferably 95% ee, more preferably more than 98% ee, and in particular preferably more than 99.5% ee.

One aspect of the present invention are compounds of formula 1 and their hydrates, solvates, salts and N-oxides, which have with regard to the chiral centers in positions 4a and 10a an absolute configuration selected from the group consisting of (4aR, 10aR), (4aS, 10aS), (4aR, 10aS) and (4aS, 10aR).

Preference is given to compounds of formula 1 and their hydrates, solvates, salts and N-oxides in which the hydrogen atoms in positions 4a and 10a are in the cis position relative to one another. The pure cis enantiomers and their mixtures in any mixing ratio and including the racemates are particularly preferred. The most preferred compounds in this context are those compounds of formula 1 and their hydrates, solvates, salts and N-oxides, which have with respect to the positions 4a and 10a the configuration shown in formula (1*):

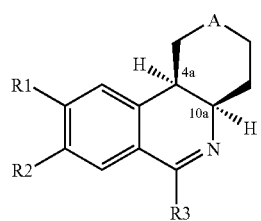

(1*)

The enantiomers can be separated in a known manner, for example, by preparing and separating corresponding diastereoisomeric compounds, by separation methods using chiral chromatography methods or by stereoselective synthesis methods. Such separation processes and synthesis methods are described, for example, in EP 247 971 and in DE 42 17 401 for hexahydrobenzo[c][1,6]naphthyridine derivatives respectively for 4-aminopiperidine derivatives. The enantiomers of formula 1 can analogously be prepared using instead of the piperidine-derivatives the corresponding tetrahydropyran derivatives.

Preferably, any mixtures of enantiomers (for example racemates) obtained during the preparation process are already separated (by formation of diastereomeric compounds, for example, salts or amides) with the help of an optical active separation agent on the stage of the 3-(3,4-dialkoxy-phenyl)-1,1-dioxohexahydro-1l$^6$-thiopyran-4-yl amines or 3-(3,4-dialkoxyphenyl-tetrahydro-thiopyran-4-ylamines (for example, intermediates B1 and B2). As suitable optical active separation agents may be mentioned, for example, optical active acids, such as for example, L-(-)- or D(+)-tartaric acid, (-)-camphanic acid, (+)-camphoric acid, D-(-)- or L-(+)-citramalic acid, (+)—O,O'-dibenzoyl-D- or (-)-O,O'-dibenzoyl-L-tartaric acid, D- or L-malic acid or R- or S-methoxyphenyl-acetic acid.

In those cases, in which A is S(O), an additional chiral center exists in position 3 of the compounds of formula 1; another aspect of the present invention are therefore compounds of formula 1 and their hydrates, solvates, salts and N-oxides, which have with regard to the chiral centers in positions 3, 4a and 10a an absolute configuration selected from the group consisting of (3R,4aR, 10aR), (3S, 4aR, 10aR), (3R,4aS, 10aS), (3S, 4aS, 10aS), (3R, 4aR, 10aS), (3S, 4aR, 10aS), (3R,4aS, 10aR) and (3S, 4aS, 10aR). Preferred are in this connection those compounds of formula 1 and their hydrates, solvates, salts and N-oxides, which have with regard to the chiral centers in positions 3, 4a and 10a an absolute configuration selected from the group consisting of (3R,4aR, 10aR) and (3S, 4aR, 10aR).

The compounds according to the invention can be prepared, for example, as shown in the reaction schemes below.

Reaction scheme 1: Reaction scheme one shows a synthesis route to compounds of formula 1, in which A has the meanings S or S(O)$_2$ and R1, R2 and R3 have the above-mentioned meanings

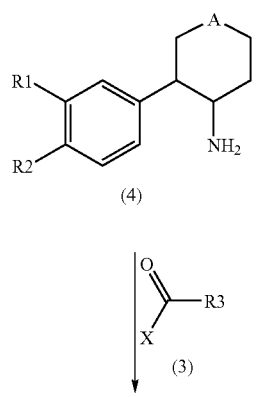

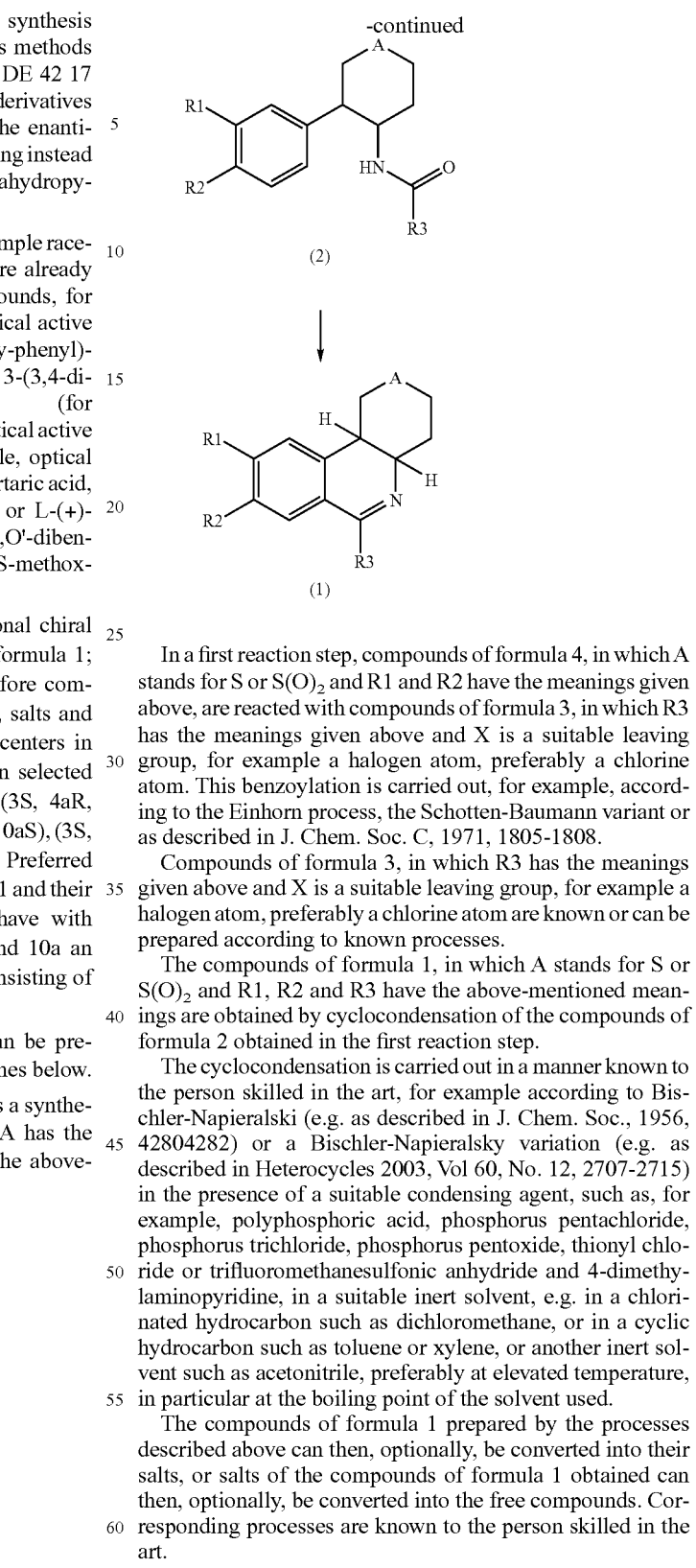

In a first reaction step, compounds of formula 4, in which A stands for S or S(O)$_2$ and R1 and R2 have the meanings given above, are reacted with compounds of formula 3, in which R3 has the meanings given above and X is a suitable leaving group, for example a halogen atom, preferably a chlorine atom. This benzoylation is carried out, for example, according to the Einhorn process, the Schotten-Baumann variant or as described in J. Chem. Soc. C, 1971, 1805-1808.

Compounds of formula 3, in which R3 has the meanings given above and X is a suitable leaving group, for example a halogen atom, preferably a chlorine atom are known or can be prepared according to known processes.

The compounds of formula 1, in which A stands for S or S(O)$_2$ and R1, R2 and R3 have the above-mentioned meanings are obtained by cyclocondensation of the compounds of formula 2 obtained in the first reaction step.

The cyclocondensation is carried out in a manner known to the person skilled in the art, for example according to Bischler-Napieralski (e.g. as described in J. Chem. Soc., 1956, 42804282) or a Bischler-Napieralsky variation (e.g. as described in Heterocycles 2003, Vol 60, No. 12, 2707-2715) in the presence of a suitable condensing agent, such as, for example, polyphosphoric acid, phosphorus pentachloride, phosphorus trichloride, phosphorus pentoxide, thionyl chloride or trifluoromethanesulfonic anhydride and 4-dimethylaminopyridine, in a suitable inert solvent, e.g. in a chlorinated hydrocarbon such as dichloromethane, or in a cyclic hydrocarbon such as toluene or xylene, or another inert solvent such as acetonitrile, preferably at elevated temperature, in particular at the boiling point of the solvent used.

The compounds of formula 1 prepared by the processes described above can then, optionally, be converted into their salts, or salts of the compounds of formula 1 obtained can then, optionally, be converted into the free compounds. Corresponding processes are known to the person skilled in the art.

In addition, the compounds of the formula 1, in which A stands for S(O)$_2$ and R1, R2 and R3 have the above mentioned meanings can be converted, optionally, into their N-oxides, for example with the aid of hydrogen peroxide in methanol or with the aid of m-chloroperoxybenzoic acid in dichloromethane. The person skilled in the art is familiar on the basis of his/her expert knowledge with the reaction conditions which are specifically necessary for carrying out the N-oxidation.

Furthermore, it is possible to convert one functional group of a compound of formula 1 to another functional group by customary methods and reactions. Thus, if desired, compounds of formula 1 with suitable functional groups can be converted into further compounds of formula 1. For instance, compounds of formula 1, in which R5 comprises an ester can be converted by acidic or alkaline saponification to the corresponding carboxylic acid or by reaction with a suitable amine to the corresponding amide.

Reaction scheme 2: In reaction scheme 2 is shown a general way for the preparation of compounds of formulae 7 and 8

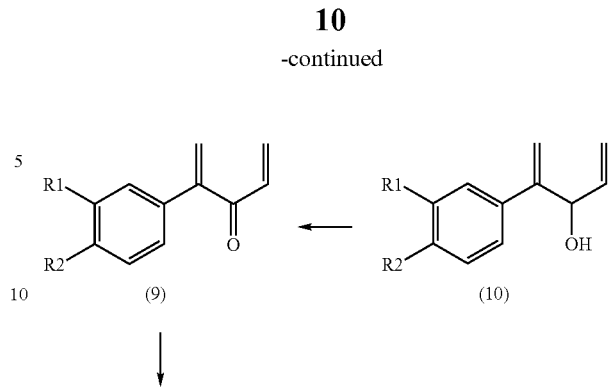

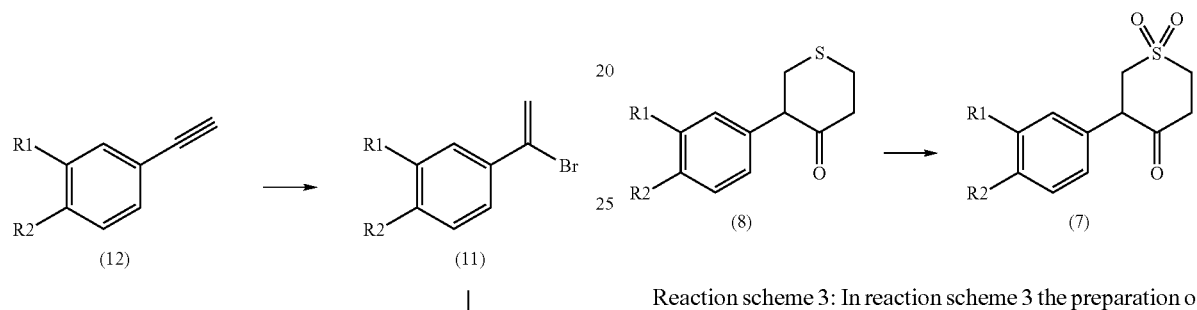

Reaction scheme 3: In reaction scheme 3 the preparation of compounds of formula 4—starting from compounds of formulae 7 and 8 is shown

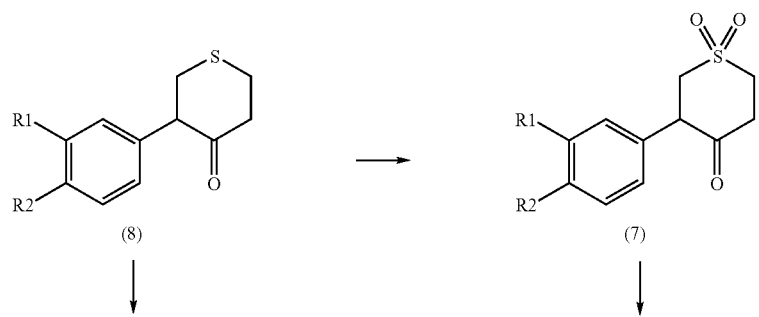

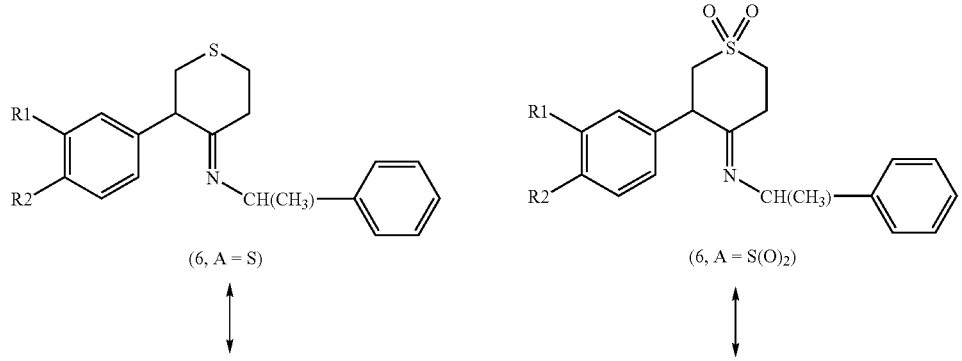

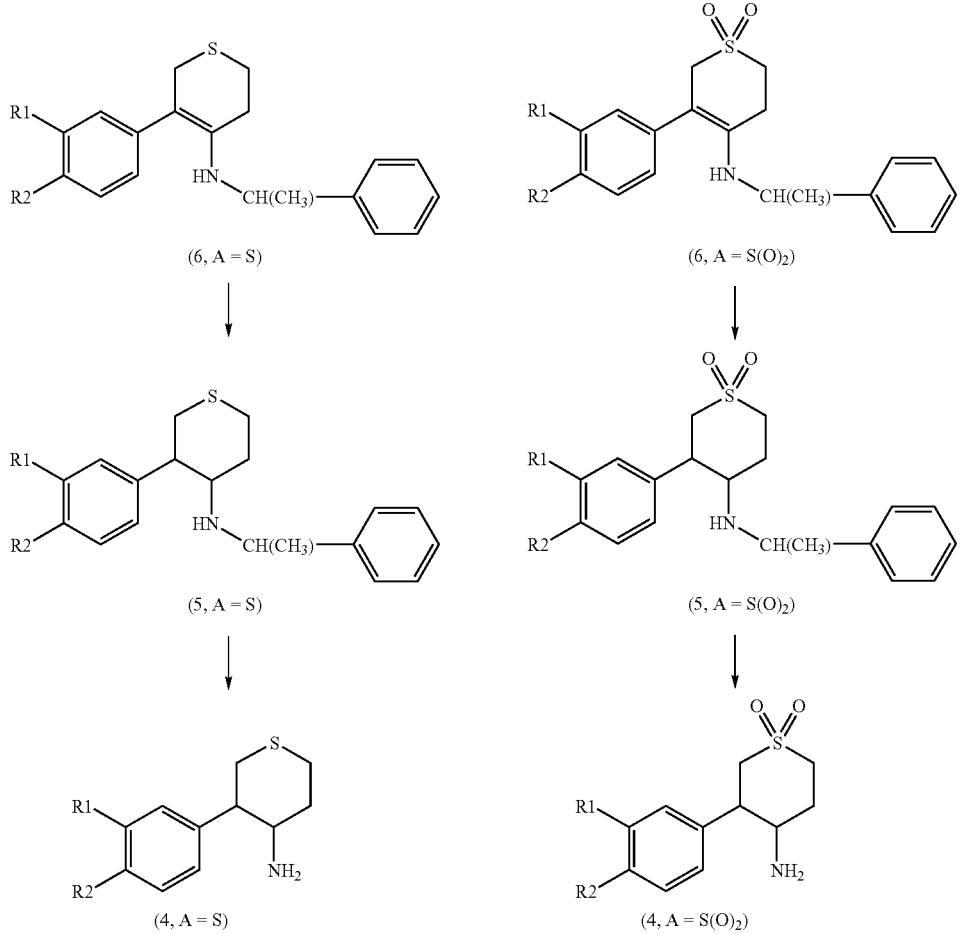

Reaction scheme 4: Reaction scheme 4 provides a method for the preparation of compounds of formula 1, in which A stands for S(O) and R1, R2 and R3 have the above-mentioned meanings

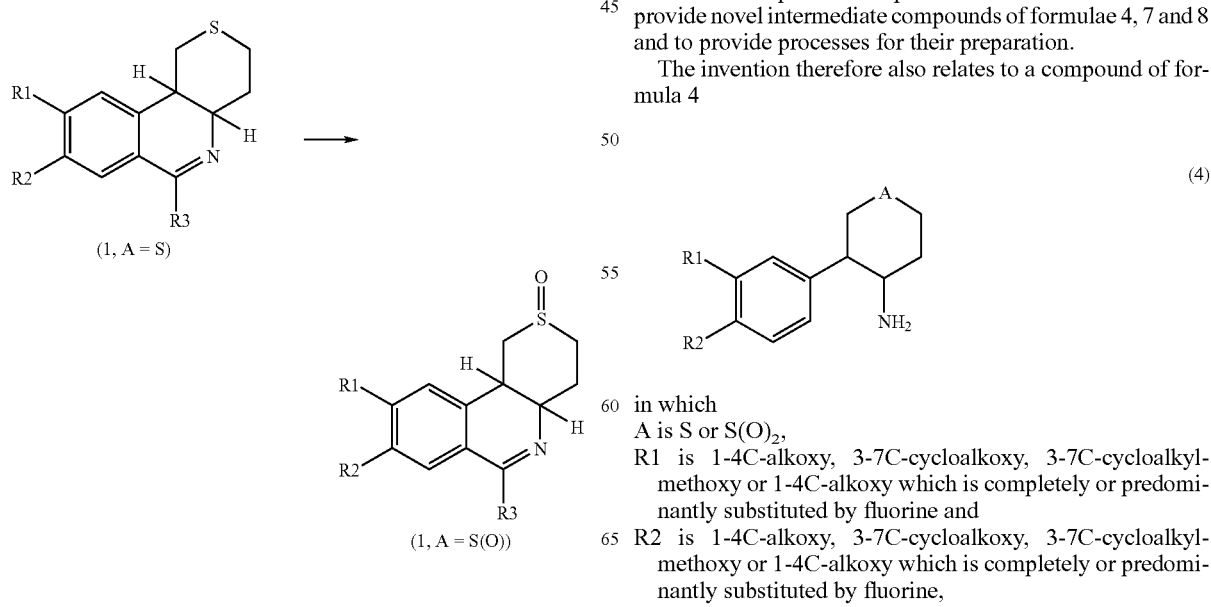

As can be seen from reaction schemes 1, 2 and 3 the compounds of formulae 4, 7 and 8 are key intermediates. They make it possible to introduce the tetrahydrothiopyran respectively the dioxotetrahydrothiopyran structure into the compounds of formula 1.

A further aspect of the present invention therefore is to provide novel intermediate compounds of formulae 4, 7 and 8 and to provide processes for their preparation.

The invention therefore also relates to a compound of formula 4

(4)

in which
A is S or S(O)$_2$,
R1 is 1-4C-alkoxy, 3-7C-cycloalkoxy, 3-7C-cycloalkyl-methoxy or 1-4C-alkoxy which is completely or predominantly substituted by fluorine and
R2 is 1-4C-alkoxy, 3-7C-cycloalkoxy, 3-7C-cycloalkyl-methoxy or 1-4C-alkoxy which is completely or predominantly substituted by fluorine, or in which
R1 and R2 together are a 1-2C-alkylenedioxy group,
or a hydrate, solvate or salt thereof, or a hydrate or solvate of a salt thereof.

A preferred compound of formula 4 is that in which
A is S or S(O)₂,
R1 is methoxy or ethoxy,
R2 is methoxy or ethoxy,
or a hydrate, solvate or salt thereof, or a hydrate or solvate of a salt thereof.

Suitable salts for compounds of formula 4 preferably are all acid addition salts. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxylbenzoyl)benzoic acid, butyric acid, sulfosalicylic acid, maleic acid, lauric acid, malic acid, fumaric acid, succinic acid, oxalic acid, tartaric acid, stearic acid, toluenesulfonic acid, methane-sulfonic acid or trifluoroacetic acid.

Furthermore, the invention relates to a compound of formula 7

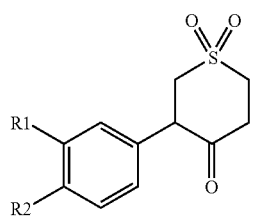

(7)

in which
R1 is 1-4C-alkoxy, 3-7C-cycloalkoxy, 3-7C-cycloalkylmethoxy or 1-4C-alkoxy which is completely or predominantly substituted by fluorine and
R2 is 1-4C-alkoxy, 3-7C-cycloalkoxy, 3-7C-cycloalkylmethoxy or 1-4C-alkoxy which is completely or predominantly substituted by fluorine,
or in which
R1 and R2 together are a 1-2C-alkylenedioxy group.

A preferred compound of formula 7 is that in which
R1 is methoxy or ethoxy and
R2 is methoxy or ethoxy.

The invention additionally relates to a compound of formula 8

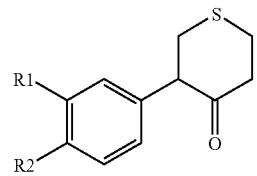

(8)

in which
R1 is 1-4C-alkoxy, 3-7C-cycloalkoxy, 3-7C-cycloalkylmethoxy or 1-4C-alkoxy which is completely or predominantly substituted by fluorine and
R2 is 1-4C-alkoxy, 3-7C-cycloalkoxy, 3-7C-cycloalkylmethoxy or 1-4C-alkoxy which is completely or predominantly substituted by fluorine,
or in which
R1 and R2 together are a 1-2C-alkylenedioxy group.

A preferred compound of formula 8 is that in which
R1 is methoxy or ethoxy and
R2 is methoxy or ethoxy.

The process for the preparation of the compounds of formula 4, in which A stands for S or S(O)₂ and R1 and R2 have the above-mentioned meanings, is characterized in that
(a) a dioxo-tetrahydro-thiopyranone derivative of formula 7 or a tetrahydro-thiopyranone derivative of formula 8

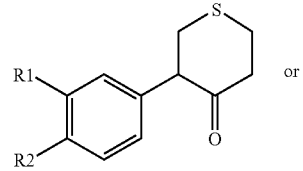

(8)

or

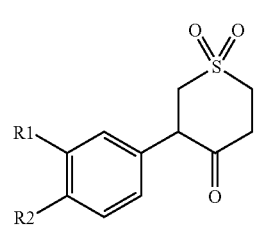

(7)

is converted with an optical pure 1-phenylethylamine to an imine/enamine of formula 6, in which A stands for S or S(O)₂ and R1 and R2 have the above-mentioned meanings

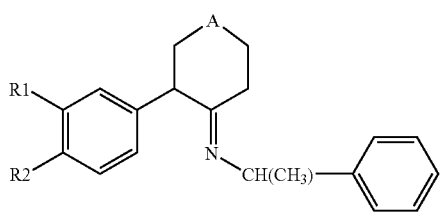

(6)

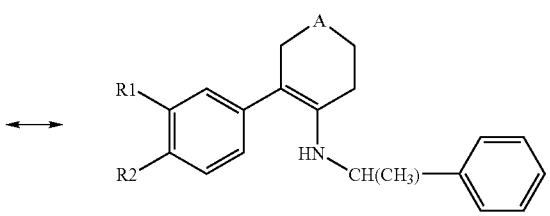

(6)

(b) hydrogenation of the obtained imine/enamine of formula 6 to a secondary amine of formula 5, in which A stands for S or S(O)$_2$ and R1 and R2 have the above-mentioned meanings

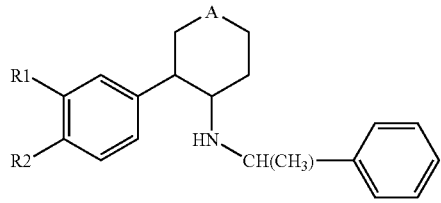

(5)

and
(c) separation of the 1-phenylethyl radical by hydrogenation, and
(d) optionally convert compounds of formula 4

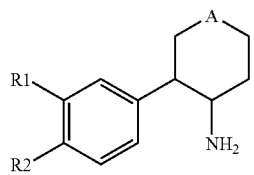

(4)

in which A stands for S or S(O)$_2$ and R1 and R2 have the above-mentioned meanings obtained in the preparation process into their salts, or convert salts of the compounds of formula 4 obtained in the preparation process then into the free compounds.

The conversion of the dioxo-tetrahydro-thiopyranone derivative of formula 7 respectively the tetrahydro-thiopyranone derivative of formula 8 with optical pure 1-phenylethylamine is carried out according to a standard procedure for condensation reactions known to the person skilled in the art, preferably in the presence of a suitable catalyst, for example p-toluenesulfonic acid, under water separation conditions in a suitable solvent, such as for example, n-hexane, benzene or toluene, at elevated temperatures, preferably at the boiling point of the solvent used.

The hydrogenation of the obtained imine/enamine of formula 6, in which A stands for S or S(O)$_2$ and R1 and R2 have the above mentioned meanings is carried out according to standard methods known to the person skilled in the art, preferably in the presence of a Raney-Nickel or a platin on carbon catalyst using an absolute alcohol, such as ethanol or methanol, as a solvent under a hydrogen pressure of about 100 mbar and at elevated temperatures, preferably between 40 and 80° C. In case, a platin on carbon catalyst is used, the conversion of the dioxo-tetrahydro-thiopyranone derivative of formula 7 and the hydrogenation of the obtained imine/enamine of formula 6 is preferably carried out as a one-pot reaction.

Alternatively, the hydrogenation of the obtained imine/enamine of formula 6, in which A stands for S and R1 and R2 have the above mentioned meanings is carried out according to methods known to the person skilled in the art, preferably in the presence of hydrogen transfer agens like alkali borohydride, alkali cyanborohydride, alkali triacetoxyborohydride or alkali acyloxyborohydrides using dichloromethane or an alcohol, such as ethanol or methanol, as a solvent at elevated temperatures, preferably between RT and 80° C. The alkali acyloxyborohydrides are prepared from NaBH$_4$ and various carboxylic acids according to methods known to the person skilled in the art, for example, as described in Tetrahedron Letters, Vol. 37, No. 23, pp 3977-3980, 1996. In case, an alkali borohydride (preferably NaBH$_4$) and a carboxylic acid (preferably 2-ethyl hexanoic acid) is used, the conversion of the dioxo-tetrahydro-thiopyranone derivative of formula 7 and the hydrogenation of the obtained imine/enamine of formula 6 is preferably carried out as a one-pot reductive amination reaction.

The separation of the 1-phenylethyl radical by hydrogenation is also carried out according to standard methods known to the person skilled in the art, preferably in the presence of 1 to 1.2 equivalents of concentrated hydrochloric acid and a palladium on carbon catalyst using an alcohol, such as methanol or ethanol as a solvent under a hydrogen pressure of about 0.1 to 10 bar, preferably 0.1 to 1 bar, and at elevated temperatures, preferably between 40 and 60° C.

The process for the preparation according to the invention yields, in case R-(+)-1-phenyl-ethylamine is used for the conversion of the dioxo-tetrahydro-thiopyranon derivative of formula 7 or the tetrahydro-thiopyranone derivatives of formula 8) the cis configurated 3-(3,4-dialkoxy-phenyl)-1,1-dioxo-hexahydro-1l$^6$-thiopyran-4-ylamines of formulae 4a and 4b, respectively the cis-configurated 3-(3,4-dialkoxy-phenyl)-tetrahydro-thiopyran-4-ylamines of formulae 4c and 4d:

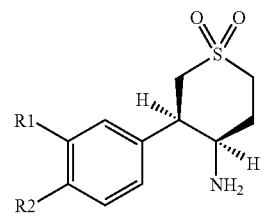

(4a)

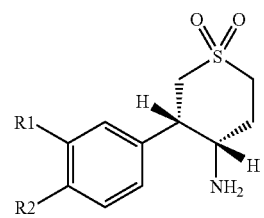

(4b)

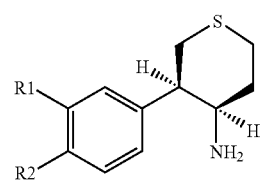

(4c)

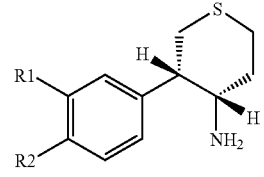

(4d)

wherein R1 and R2 have the above-mentioned meanings. The cis-configurated 3-(3,4-dialkoxy-phenyl)-1,1-dioxo-hexahydro-1l$^6$-thiopyran-4-ylamine of formulae 4a and 4b and the 3-(3,4-dialkoxy-phenyl)-tetrahydro-thiopyran-4-ylamine of formulae 4c and 4d are novel and also part of the invention.

The expression "optical pure 1-phenylethylamine" mentioned in the above paragraph means that R-(+)-1-phenylethylamine or S(-)-1-phenyl-ethylamine, preferably R-(+)-1-phenyl-ethylamine is used in reaction step (a). R-(+)-1-phenyl-ethylamine and S(-)-1-phenyl-ethylamine are commercially available with 99% ee.

Preferred 3-(3,4-dialkoxy-phenyl)-1,1-dioxo-hexahydro-1l$^6$-thiopyran-4-ylamine of formulae 4a and 4b are those, in which R1 is methoxy or ethoxy and R2 is methoxy or ethoxy. Particularly preferred are the 3-(3,4-dialkoxy-phenyl)-1,1-dioxo-hexahydro-1l$^6$-thiopyran-4-ylamine of formula 4a in which R1 is methoxy or ethoxy and R2 is methoxy or ethoxy.

Preferred 3-(3,4-dialkoxy-phenyl)-tetrahydro-thiopyran-4-ylamine of formulae 4c and 4d are those, in which R1 is methoxy or ethoxy and R2 is methoxy or ethoxy. Particularly preferred are the 3-(3,4-dialkoxy-phenyl)-tetrahydro-thiopyran-4-ylamine of formula 4c in which R1 is methoxy or ethoxy and R2 is methoxy or ethoxy.

The process for the preparation of the compounds of formula 8 is characterized in that (a) compounds of formula 12

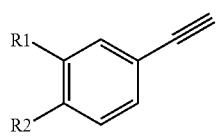

(12)

are reacted with concentrated hydrobromic acid under strictly anhydrous conditions, (b) the resulting 1-bromo-1-(3,4-dialkoxyphenyl)ethane derivatives of formula 11

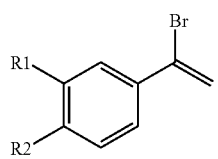

(11)

are subjected to a bromo-lithium exchange reaction and then are converted with acrolein to yield 2-(3,4-dialkoxyphenyl)-1,4-pentadien-3-ol derivatives of formula 10

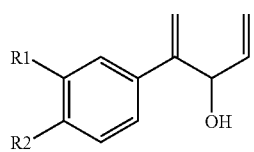

(10)

(c) oxidation of the 2-(3,4-dialkoxyphenyl)-1,4-pentadien-3-ol derivatives of formula 10 to the corresponding and 2-(3,4-dialkoxyphenyl)-1,4-pentadien-3-one derivatives of formula 9

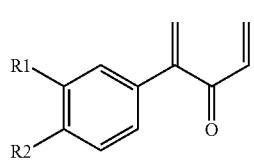

(9)

(d) and converting the 2-(3,4-dialkoxyphenyl)-1,4-pentadien-3-one derivatives of formula 9 to 3-(3,4-dialkoxy-phenyl)-tetrahydro-thiopyran-4-one derivatives of formula 8 via a double Michael addition with Na$_2$S or NaHS, wherein in the compounds of formulae 8, 9, 10, 11 and 12, R1 and R2 have the above-mentioned meanings.

The conversion of the compounds of formula 12 with hydrobromic acid is carried out under strictly anhydrous conditions. Preferably a high quality HBr solution in glacial acetic acid is used for the conversion. The bromo-lithium exchange reaction is carried out under standard conditions with t-BuLi in tetrahydrofurane at −78° C. Preferably freshly distilled acrolein is used for the conversion to the 2-(3,4-dialkoxyphenyl)-1,4-pentadien-3-ol derivatives of formula 10.

The oxidation of the 2-(3,4-dialkoxyphenyl)-1,4-pentadien-3-ol derivatives of formula 10 is carried out using standard oxidation methods, such as for example the Swern oxidation, or by using MnO$_2$ as an oxidation agent. In case, MnO$_2$ is used as an oxidation agent, it is used in large excess of about 20-25 equivalents.

The conversion of the 2-(3,4-dialkoxyphenyl)-1,4-pentadien-3-one derivatives of formula 9 to 3-(3,4-dialkoxy-phenyl)-tetrahydro-thiopyran-4-one derivatives of formula 8 preferably is carried out using about 2.0 equivalents of NaHS×9H$_2$0 in 2-methoxyethanol as solvent at elevated temperature, preferably between 30 and 50° C., more preferably at about 40° C.

Alternatively, the conversion of the 2-(3,4-dialkoxyphenyl)-1,4-pentadien-3-one derivatives of formula 9 to 3-(3,4-dialkoxy-phenyl)-tetrahydro-thiopyran-4-one derivatives of formula 8 can be carried out using 1.5-2.0 equivalents of Na$_2$S×9H$_2$0 in a tetrahydrofuran/water (1:1 v/v) mixture at elevated temperature, preferably between 40 and 60° C., more preferably at about 55° C.

The above-described process for the preparation yields racemic 3-(3,4-dialkoxy-phenyl)-tetrahydro-thio-pyran-4-one derivatives of formula 8, wherein R1 and R2 have the above-mentioned meanings.

The 3-(3,4-dialkoxy-phenyl)-tetrahydro-thiopyran-4-one derivatives of formula 8 are novel and also part of the invention. Preferred 3-(3,4-dialkoxy-phenyl)-tetrahydro-thiopyran-4-one derivatives of formula 8 are those in which R1 is methoxy or ethoxy and R2 is methoxy or ethoxy.

The process for the preparation of compounds of formula 7 is characterized in that compounds of formula 8 are oxidized to yield compounds of formula 7.

All oxidation agents known to the person skilled in the art for the conversion of sulfides to sulfones can be used in this oxidation process, such as for example KMnO$_4$ (J. Org. Chem. 1980, 3634-3639), meta-chlorperbenzoic acid (J. Org. Chem. 1988, 3125-3127) or hydrogen peroxide together with methyltrioxo-rhenium (Bull. Chem. Soc. Jp. 1996, 2955-2960). Preferably hydrogen peroxide in acetic acid is used in the oxidation process.

The compounds of formula 7 are new and also part of the invention. Preferred are those compounds of formula 7, in which R1 is methoxy or ethoxy and R2 is methoxy or ethoxy.

Compounds of formula 12 can, for example, be prepared according to Reaction Scheme 5:

Reaction scheme 5:

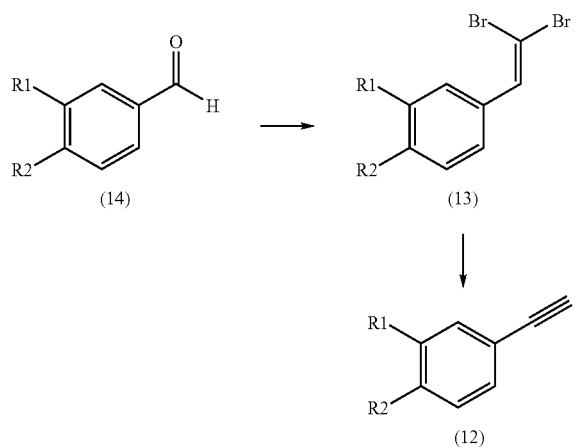

In a first reaction step starting from dialkoxybenzaldehydes of formula 14, wherein R1 and R2 have the above-mentioned meanings, 2,2-dibromo-1-(3,4-dialkoxyphenyl)ethene derivatives of formula 13 are pre-pared according to the Corey-Fuchs procedure (see for example Tetrahedron Letters 1972, 36, 3769-3772). In a subsequent elimination step the 2,2-dibromo-1-(3,4-dialkoxyphenyl)ethene derivatives of formula 13 are converted to dialkoxyphenylacetylene derivatives of formula 12.

Additional experimental details for the preparation of compounds of formula 12 are given in the section Examples/Starting Materials.

Compounds of formula 1, in which A stands for S(O) and R1, R2 and R3 have the above-mentioned meanings are preferably prepared starting from the corresponding compounds of formula 1, in which A stands for S by an oxidation reaction.

Suitable oxidation agents are for example $H_2O_2$ with or without methyltrioxorhenium, $NaIO_4$, halogen arylperacids, preferably m-chloroperbenzoic acid using a chlorinated hydrocarbon, such as methylene chloride or chloroform, or a low molecular weight aliphatic alcohol, such as methanol, ethanol or isopropanol as a solvent and at temperatures preferably between –50° C. and RT.

Starting from compounds of formula 1, which have with regard to the chiral centers in positions 4a and 10a the configuration (4aR, 10aR), one obtains two sulfoxide diastereomers [configuration: (3R,4aR, 10aR) and (3S, 4aR, 10aR)] which can be separated, for example, by column chromatography.

If desired, the sulfoxide diastereomers of formula 1 can be further oxidized to yield the corresponding sulfones of formula 1, respectively the corresponding N-oxides of the sulfones of formula 1.

It is also known to the person skilled in the art that, if a plurality of reactive centers are present in a starting material or intermediate, it may be necessary to temporarily block one or more reactive centers with protective groups so that a reaction takes place only at the desired reactive center. A detailed description of how to use a large number of proven protective groups can be found, for example, in T. W. Greene, Protective Groups in Organic Synthesis, John Wiley & Sons, 1991.

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

Salts of the compounds according to the invention can be obtained by dissolving the free compound in a suitable solvent (for example a ketone, such as acetone, methylethylketone or methylisobutylketone, an ether, such as diethyl ether, tetrahydrofuran or dioxane, a chlorinated hydrocarbon, such as methylene chloride or chloroform, or a low molecular weight aliphatic alcohol, such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom.

The salts are obtained by filtering, reprecipitating, precipitating with a non-solvent for the salt or by evaporating the solvent. Salts obtained can be converted into the free compounds which, in turn, can be converted into salts. In this manner, pharmaceutically inacceptable salts, which can be obtained, for example, as process products during the preparation of the compounds according to the invention on an industrial scale, can be converted into pharmaceutically acceptable salts by processes known to the person skilled in the art.

The following examples illustrate the invention in greater detail, without restricting it. As well, further compounds of formula 1, of which the preparation is explicitly not described, can be prepared in an analogous or similar manner as is evident to a person skilled in the art.

In the examples, h stands for hour(s) and RT for room temperature, PE for petrolether, EE for ethyl acetate, $SiO_2$ for Silica gel, TLC for thin layer chromatography and THF for tetrahydrofurane. The compounds mentioned in the examples as well as the hydrates, solvates or salts, hydrates or solvates of a salt, N-oxide or salt, hydrate or solvate of a N-oxide thereof are a preferred subject of the invention.

EXAMPLES

End Products 1. 4-((4aR,10aR)-6-Ethoxy-7-methoxy-1,4,4a,10a-tetrahydro-2H-3-thia-10-aza-phenanthren-9-yl)-N,N-diisopropyl-benzamide

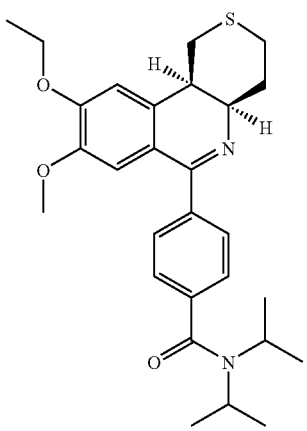

5 mmol of N-[(3R,4R)-3-Ethoxy-4-methoxy-phenyl)-tetrahydro-thiopyran-4-yl]-N',N'-diisopropyl-terephthalamide are heated to boiling under reflux for 4 h in 25 ml of acetonitrile and 3 ml of phosphorus oxytrichloride. After distilling off the excess of phosphorus oxytrichloride and acetonitrile, the residue is partitioned between dichloromethane and saturated sodium hydrogencarbonate solution. The organic phase is washed with water, dried over sodium sulfate and concentrated. The solid residue is purified by column chromatography on $SiO_2$ (isopropyl acetate/n-hexane/triethyl amine 1/8/1 vol/vol/vol), the main product fraction is separated and concentrated yielding the title compound as grayish solid foam. A solution of this residue is dissolved in a mixture of 3 ml dioxane and 3 ml water and the solution is lyophilized yielding the title compound as white powdered solid. M.p. 84-89% (unsharp, enamel-like shrinking starting at about 80° C.).

Alternatively, a solution of 12.5 mmol of trifluoromethanesulfonic anhydride dissolved in 10 ml dichloro-methane is added over a periode of 20 min to a cooled (ice-water bath) solution of 2.5 mmol of N-[(3R,4R)-3-Ethoxy-4-methoxy-phenyl)-tetrahydro-thiopyran-4-yl]-N',N'-diisopropyl-terephthalamide and 7.5 mmol of 4-dimethylamino-pyridine in 30 ml of dichloromethane. The solution is stirred over night and then added to a cooled (ice-water bath) mixture of 10 ml of methanol, 10 ml of triethyl amine and 20 ml of dichloromethane and the mixture is stirred for 1 h. After concentration under reduced pressure the solid residue is purified by column chromatography on $SiO_2$ (isopropyl acetate/n-hexane/triethyl amine 1/8/1 vol/vol/vol), the main product fraction is separated and concentrated yielding the title compound as grayish solid foam. A solution of this residue is dissolved in a mixture of 3 ml dioxane and 3 ml water and the solution is lyophilized yielding the title compound as white powdered solid. M.p. 84-89° C. (unsharp, enamel-like shrinking starting at about 80° C.).

MS: calc.: $C_{28}H_{36}N_2O_3S$ (480.67) fnd.: [M+1] 481.3

2. 4-((4aR,10aR)-6-Ethoxy-7-methoxy-3-oxo-1,2,3,4,4a,10a-hexahydro-3l$^4$-thia-10-aza-phenanthren-9-yl)-N,N-diisopropyl-benzamide (Diastereomer A)

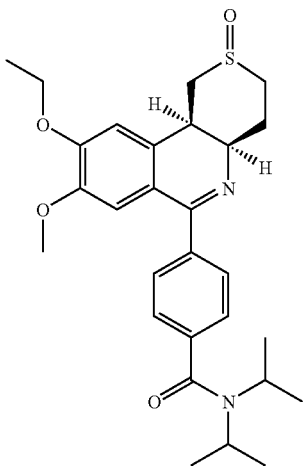

During a periode of 30 min a solution of 1.2 mmol meta-chloroperbenzoic acid (70%) in 10 ml of di-chloromethane is dropped into a at −40° C. cooled solution of 0.4 mmol of 4-((4aR,10aR)-6-Ethoxy-7-methoxy-1,4,4a,10a-tetrahydro-2H-3-thia-10-aza-phenanthren-9-yl)-N,N-diisopropyl-benzamide in 10 ml of dichloromethane. The mixture is stirred at −40° C. for about 1 h and poured into a mixture of 25 ml of 10% $Na_2S_2O_3$ solution in water and 25 ml saturated brine solution. The aqueous mixture is extracted three times with dichloromethane, the collected organic phases are washed with saturated brine solution and then with water. The separated and combined organic phase is dried over sodium sulphate and filtered off. The filtrate is concentrated and the solid residue purified by column chromatography on $SiO_2$ (isopropyl acetate/r-hexane/triethyl amine 6/3/1 vol/vol/vol). Two pure main product fractions are separated. The first washed out pure main product fraction is concentrated yielding the diastereomer A compound as grayish solid foam. A solution of this residue in tert-butanol is lyophilized yielding the title compound as white powdered solid. M.p. 60-65° C. (unsharp, enamel-like shrinking starting at about 53° C.).

MS: calc.: $C_{28}H_{36}N_2O_4S$ (496.67) fnd.: [M+1] 497.2

3. 4-((4aR,10aR)-6-Ethoxy-7-methoxy-3-oxo-1,2,3,4,4a,10a-hexahydro-3l$^4$-thia-10-aza-phenanthren-9-yl)-N,N-diisopropyl-benzamide (Diastereomer B)

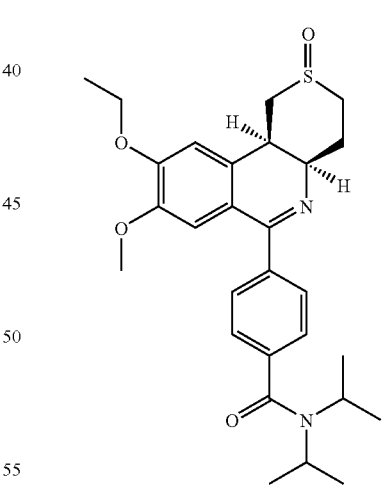

The second washed out pure main product fraction from the chromatography of example 2 is concentrated yielding the diastereomer B compound as grayish solid foam. A solution of this residue in tert-butanol is lyophilized yielding the title diastereomer B compound as white powdered solid. M.p. 80-85° C. (unsharp, enamel-like shrinking and brownish discolouration starting at about 75° C.).

MS: calc.: $C_{28}H_{36}N_2O_4S$ (496.67) fnd.: [M+1] 497.2

4. 4-((4aR,10aR)-6-Ethoxy-7-methoxy-3,3-dioxo-1,2,3,4,4a,10a-hexahydro-3l⁶-thia-10-aza-phenanthren-9-yl)-N,N-diisopropyl-benzamide

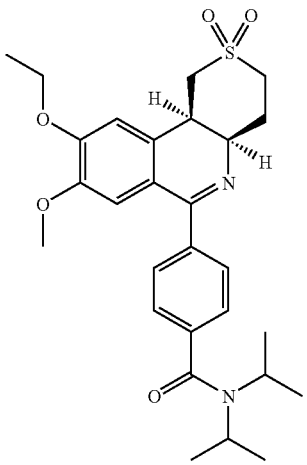

During a periode of 30 min a solution of 0.64 mmol meta-chloroperbenzoic acid (70%) in 10 ml of dichloromethane is dropped at RT into a solution of 0.2 mmol 4-((4aR,10aR)-6-Ethoxy-7-methoxy-3-oxo-1,2,3,4,4a,10a-hexahydro-3l⁴-thia-10-aza-phenanthren-9-yl)-N,N-diisopropyl-benzamide (mixture fraction of diasteromer A and B from the chromatography of example 2) in 10 ml of dichloromethane. The mixture is stirred at RT for about 1 h and poured into a mixture of 25 ml of 10% Na₂S₂O₃ solution in water and 25 ml saturated brine solution. The aqueous mixture is extracted three times with dichloromethane, the collected organic phases are washed with saturated brine solution and then with water. The separated and combined organic phase is dried over sodium sulphate and filtered off. The filtrate is concentrated and the solid residue purified by column chromatography on SiO₂ (isopropyl acetate/n-hexane/triethyl amine gradient from 6/3/1 vol/vol/vol to 0/9/1 vol/vol/vol). Two pure main product fractions are separated. The first washed out pure main product fraction is concentrated yielding the title compound as grayish solid foam. A solution of this residue is dissolved in tert-butanol and the solution is lyophilized yielding the title compound as white powdered solid. M.p. 90-95° C. (unsharp, enamel-like shrinking starting at about 80° C.).

Alternative synthesis 1: 5 mmol of N-[(3R,4R)-3-(3-Ethoxy-4-methoxy-phenyl)-tetrahydro-pyran-4-yl]-N',N'-diisopropyl-terephthalamide are heated to boiling under reflux for 4 h in 25 ml of acetonitrile and 3 ml of phosphorus oxytrichloride. After distilling off the excess of phosphorus oxytrichloride and acetonitrile, the residue is partitioned between dichloromethane and saturated sodium hydrogencarbonate solution. The organic phase is washed with water, dried over sodium sulfate and concentrated. The further purification is carried out as described above.

Alternative synthesis 2: A solution of 12.5 mmol of triflouoromethanesulfonic anhydride dissolved in 10 ml dichloromethane is added over a periode of 20 min to a cooled (ice-water bath) solution of 2.5 mmol of N-[(3R,4R)-3-(3-Ethoxy-4-methoxy-phenyl)-tetrahydro-pyran-4-yl]-N',N'-diisopropyl-terephthalamide and 7.5 mmol of 4-dimethylamino-pyridine in 30 ml of dichloromethane. The solution is stirred over night and then added to a cooled (ice-water bath) mixture of 10 ml of methanol, 10 ml of triethyl amine and 20 ml of d-chloromethane and the mixture is stirred for 1 h. After concentration under reduced pressure the solid residue is purified as described above.

MS: calc.: $C_{28}H_{36}N_2O_5S$ (512.67) fnd.: [M+1] 513.3

5. 4-((4aR,10aR)-6-Ethoxy-7-methoxy-3,3-dioxo-10-oxy-1,2,3,4,4a,10a-hexahydro-3l⁶-thia-10-aza-phenanthren-9-yl)-N,N-diisopropyl-benzamide

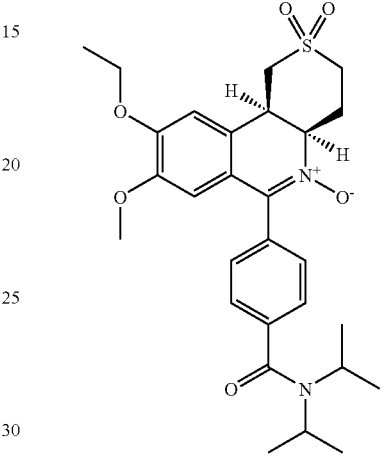

The second washed out pure main product fraction from the chromatography of example 4 is concentrated yielding the title compound as grayish solid foam. A solution of this residue is dissolved in tert-butanol and the solution is lyophilized yielding the title compound as white powdered solid. M.p. 145-149° C. (unsharp, enamel-like shrinking starting at about 125° C.).

MS: calc.: $C_{28}H_{36}N_2O_6S$ (528.67) fnd.: [M+1] 529.3

Starting Materials

A1. N-[(3R,4R)-3-(3-ethoxy-4-methoxy-phenyl)-1,1-dioxo-hexahydro-1l⁶-thiopyran-4-yl]N',N'-diisopropyl-terephthalamide

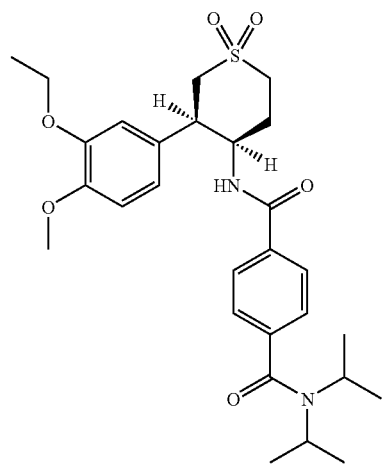

A solution of 1 equivalent 4-diisopropylcarbamoyl-benzoyl chloride (prepared from N,N-diisopropyl-terephthalamic acid and thionyl chloride) in dichloromethane is added dropwise at RT in the course of 10 min. to a solution of 1 equivalent of (3R,4R)-3-(3-ethoxy-4-methoxy-phenyl)-1,1-dioxo-1l$^6$-hexahydro-thiopyran-4-ylamine in dichloromethane and 1,1 equivalents of triethylamine. After stirring for about 2 h, the mixture is extracted with saturated sodium hydrogencarbonate solution, and the organic phase is washed a further two times with water and dried over sodium sulfate. The viscous residue remaining after concentration is purified by column chromatography on silica gel or aluminium oxide. The main product fraction concentrated in vacuo affords a solid foaming residue.

A2. N-[(3R,4R)-3-Ethoxy-4-methoxy-phenyl)tetrahydro-thiopyran-4-yl]-N',N'-diisopropyl-terephthalamide

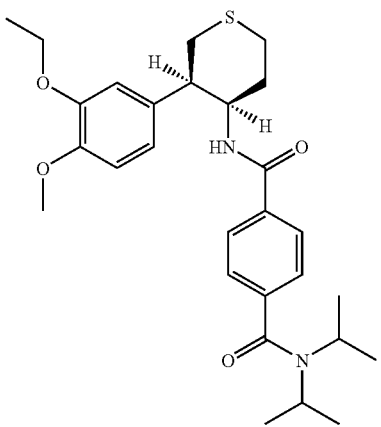

A solution of 4 mmol of 4-diisopropylcarbamoyl-benzoyl chloride (prepared from N,N-diisopropylterephthalamic acid and thionyl chloride) in 10 ml of dichloromethane is added dropwise at RT in the course of 10 min. to a solution of 236 mmol of (3R,4R)-3-(3-ethoxy-4-methoxy-phenyl)-tetrahydro-2H-thiopyran-4-amine in 10 ml of dichloromethane and 1.1 equivalents of triethylamine. After stirring for about 2 h, the mixture is extracted with saturated sodium hydrogencarbonate solution, and the organic phase is washed a further two times with water and dried over sodium sulfate. The viscous residue remaining after concentration is purified by column chromatography on SiO$_2$ (isopropyl acetate/n-hexane/triethyl amine 2/7/1 vol/vol/vol). The main product fraction is concentrated yielding the title compound as grayish resinous solid, which is used for the next reactions without further treatment.

MS: calc.: $C_{28}H_{36}N_2O_4S$ (498.69) fnd.: [M+1] 499.3

B1. (3R,4R)-3-(3-Ethoxy-4-methoxy-phenyl-1,1-dioxo-1l$^6$-hexahydro-thiopyran-4-ylamine

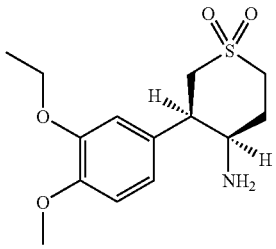

A suspension of 50 mmol of 3-(3-ethoxy-4-methoxy-phenyl)-1,1-dioxo-tetrahydro-1l$^6$-thiopyran-4-one, 75 mmol of (R)-(+)-1-phenylethyl amine, 5 mmol of p-toluenesulfonic acid mono-hydrate and 1 g of platin-on-carbon catalyst (3% Pt) in 400 ml of absolute methanol is hydrogenated at 60° C. and 100 mbar hydrogen pressure until no further ketone can be detected by TLC. After cooling to RT the suspension is filtered over a tonsil layer and the filtrate is concentrated under vacuum. The viscous residue is partitioned between dichloromethane and 20% citric acid solution. The pH of the aqueous phase is neutralized to about 6.0 with diluted sodium hydroxide solution and the aqueous phase is extracted 4 times with dichloromethane. The combined organic phases are dried over sodium sulfate and concentrated under vacuum yielding [(3R,4R)-3-(3-ethoxy-4-methoxy-phenyl)-1,1-dioxo-1l$^6$-hexahydro-thiopyran-4-yl]-((R)-1-phenyl-ethyl)-amine as main compound. The viscous residue is not further purified and used for the next step as raw product as it is. The viscous residue is dissolved in 1.2 equivalent of 37% hydrochloric acid and methanol and palladium-on-carbon catalyst is added. The slurry is hydrogenated at 60° C. and 100 mbar hydrogen pressure until no further [(3R,4R)-3-(3-ethoxy-4-methoxy-phenyl)-1,1-dioxo-1l$^6$-hexahydro-thiopyran-4-yl]-((R)-1-phenyl-ethyl)-amine can be detected by TLC. After cooling to RT the suspension is filtered over a tonsil layer and the filtrate is concentrated under vacuum. The viscous residue is purified by silica gel or aluminium oxide chromatography. The main product fraction is concentrated in vacuo and affords the title compound as solid foaming residue.

Alternatively, 3-(3-ethoxy-4-methoxy-phenyl)-1,1-dioxo-tetrahydro-1l$^6$-thiopyran-4-one can be converted to (3R,4R)-3-(3-ethoxy-4-methoxy-phenyl)-1,1-dioxo-1l$^6$-hexahydro-thiopyran-4-ylamine applying the processes described in DE4217401 for the preparation of cis-(−)-4-amino-3-(3,4-dimethoxyphenyl)-1-methyl-piperidine.

B2. (3R,4R)-3-(3-Ethoxy-4-methoxy-phenyl)-tetrahydro-thiopyran-4-ylamine hydrochloride

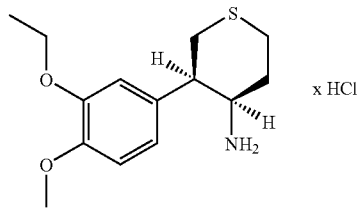

A mixture of 3.6 g of 10% Pd catalyst on charcoal and 4 mmol of (3R,4R)-3-(3-ethoxy-4-methoxyphenyl)-N-[(1R)-1-phenylethyl]tetrahydro-2H-thiopyran-4-amine hydrochloride in 100 ml of methanol is hydrogenated with 110 mbar hydrogen pressure at reflux temperature for 5 h. Additional 3.6 g of the Pd catalyst are added and the hydrogenation is continued for further 5 h. The catalyst is filtered off and the filtrate concentrated yielding the title compound as a highly viscous resin which is used for the next reaction steps without further purification.

MS: calc.: $C_{14}H_{21}NO_2S$ (free base) (267.85) fnd.: [M+1] 268.1

B3. [(3R,4R)-3-(3-Ethoxy-4-methoxy-phenyl)-tetrahydro-thiopyran-4-yl]((R)-1-phenyl-ethyl)-amine hydrochloride

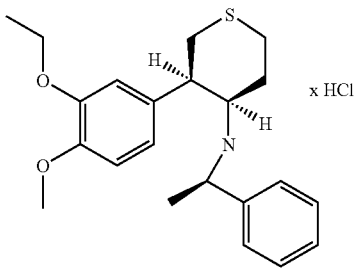

A solution of 70 mmol of 2-methyl-hexanoic acid in 20 ml of dichloromethane is dropped into a slurry of 20 mmol of NaBH$_4$ in 80 ml of dichloromethane at RT over a period of 2 h. Following further agitation of the slurry for about 2 h a solution of 10 mmol of 3-(3-ethoxy-4-methoxy-phenyl)-tetrahydro-thiopyran-4-one and 15 mmol of R-(+)-1-phenyl-ethyl amine in 20 ml of dichloromethane is dropped into the slurry at RT over a period of 30 min and the mixture is stirred over night. The mixture is extracted with 10% sodium hydroxide solution, and the organic phase is washed further two times with water and dried over sodium sulfate. The viscous residue remaining after concentration is purified by column chromatography on SiO$_2$ (isopropyl acetate/n-hexane/triethyl amine 5/4/1 vol/vol/vol). A solution of about 1.2 equivalents of HCl in isopropanol is added to the main product fraction and the mixture is concentrated in vacuo yielding the title compound as grayish solid foam. M.p. 122-126° C. (unsharp, decomposition, enamel-like shrinking starting at about 85° C.).

MS: calc.: C$_{22}$H$_{29}$NO$_2$S (free base) (371.55) fnd.: [M+1] 372.1

C. 3-(3-Ethoxy-4-methoxy-phenyl)-1,1-dioxo-tetrahydro-1l$^6$-thiopyran-4-one

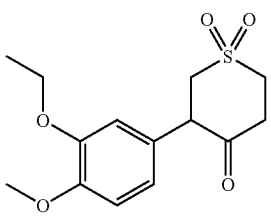

To a solution of 3-(3-ethoxy-4-methoxy-phenyl)-tetrahydro-thiopyran-4-one (0.08 mmol) in HOAc (0.2 ml) is added H$_2$O$_2$ (0.05 ml, 1.6 mmol), and the reaction mixture is stirred at 80° C. for 2 h. After addition of CH$_2$Cl$_2$ (10 ml), the reaction mixture is washed with H$_2$O (20 ml). The layers are separated, and the organic layer is dried (MgSO$_4$) and concentrated. Chromatography on silica gel yields the title compound.

General procedure A for the preparation of 3-aryl-tetrahydrothiopyran-4-ones [Compounds of Formula (8)]

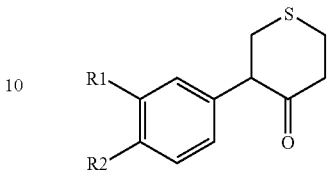

A1: Na$_2$S×9H$_2$O (1.5-2 equiv.) is added to a solution of a 2-aryl-1,4-pentadien-3-one derivative (1 equiv.) in THF/H$_2$O (1:1) (8 l/mol). The reaction mixture is stirred at 55° C. for 3 h and then poured on water (35 l/mol). The resulting mixture is extracted with Et$_2$O or EE (250 l/mol). The combined organic layers are washed with a saturated aqueous solution of NaCl (50 l/mol) and dried (MgSO$_4$). After removal of all volatile materials under vacuum, the residue is chromatographed on SiO$_2$ to give the corresponding 3-aryl-tetrahydrothiopyran-4-ones.

Alternative route A2: NaHS×9H$_2$O (2 eqiuv.) is added to a solution of 2-aryl-1,4-pentadien-3-one derivative (1 equiv.) in 2-methoxyethanol (3 ml). The reaction mixture is stirred at 40° C. for 28 h and then poured onto water (15 ml). After extraction with EE (3×20 ml) the combined organic layers are washed with water (10 ml), dried (MgSO$_4$), and all volatile materials removed under vacuum. Chromatography of the residue on SiO$_2$ (PE/EE 5:1) give the corresponding 3-aryl-tetrahydrothiopyran-4-ones.

D1. 3-(3-Ethoxy-4-methoxy-phenyl)-tetrahydro-thiopyran-4-one

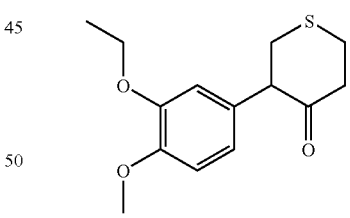

According to the General Procedure A1, Na$_2$S 9H$_2$O (92 mg, 0.39 mmol) and 2-(3-Ethoxy-4-methoxy-phenyl)-1,4-pentadien-3-one (50 mg, 0.22 mmol) are converted to give after workup and chromatography (SiO$_2$, PE/EE 2:1, R$_f$=0.31) the title compound (40 mg, 0.15 mmol) as a colorless solid.

$^1$H NMR (300 MHz, CDCl$_3$): δ=1.46 (t, J=7.0 Hz, 3H; CH$_3$), 2.76-2.92 (m, 2H), 2.98-3.17 (m, 3H), 3.24 (dd, J=13.6 Hz, J=10.6 Hz, 1H), 3.86 (s, 3H), 3.90 (dd, J=10.6 Hz, J=4.8 Hz, 1H), 4.04-4.13 (m, 2H), 6.71 (d, J=1.9 Hz, 1H), 6.74 (dd, J=8.2 Hz, J=2.0 Hz, 1H), 6.85 (d, J=8.2 Hz, 1H) ppm.

Anal. calcd. for C$_{14}$H$_{18}$O$_3$S (266.35): C 61.13, H 6.81; found C 62.81, H 6.89.

D2. 3-(3,4-Dimethoxy-phenyl)-tetrahydro-thiopyran-4-one

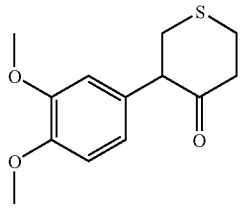

According to the General Procedure A1, Na$_2$S.9H$_2$O (42 mg, 0.18 mmol) and 2-(3,4-dimethoxy-phenyl)-1,4-pentadien-3-one (20 mg, 0.09 mmol) are converted to give after workup and chromatography (SiO$_2$, PE/EE 2:1, R$_f$=0.26) the title compound (11 mg, 0.04 mmol, 48%) as a colorless solid; C$_{13}$H$_{16}$O$_3$S (252.33).

$^1$H NMR (250 MHz, CDCl$_3$): δ=2.83-2.88 (m, 2H), 3.03-3.13 (m, 3H), 3.25 (dd, J=13.5 Hz, J=10.7 Hz), 3.87 (s, br., 6H, 2×OCH$_3$), 3.92 (dd, J=10.6 Hz, J=4.8 Hz, 1H), 6.69-6.77 (m, 2H), 6.83-6.87 (m, 1H) ppm.

General Procedure B for the Preparation of 2-aryl-1,4-pentadien-3-ones [Compounds of Formula (9)]

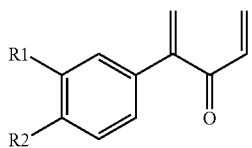

MnO$_2$ (20-25 equiv.) is added portionwise to a solution of a 2-aryl-1,4-pentadien-3-ol derivative (1 equiv.) in CH$_2$Cl$_2$ (12 l/mol). After being stirred for 35-60 min at RT, the reaction mixture is filtered through SiO$_2$ to separate MnO$_2$, which is washed several times with EE. The filtrate is concentrated and the residue chromatographed on SiO$_2$ to give the corresponding 2-aryl-1,4-pentadien-3-one derivative. The 2-aryl-1,4-pentadien-3-one derivatives are not stable and decompose even at −15° C. within a few days; preferably they are converted in further synthetic procedures within hours.

E1. 2-(3-Ethoxy-4-methoxy-phenyl)-1,4-pentadien-3-one

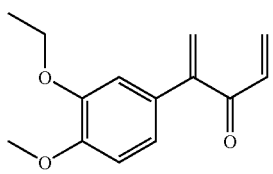

According to the General Procedure B, MnO$_2$ (1.63 g, 18.70 mmol) and 2-(3-ethoxy-4-methoxyphenyl)-1,4-pentadien-3-ol (200 mg, 0.85 mmol) are converted to give after workup and chromatography (SiO$_2$, PE/EE=2:1, R$_f$=0.40) the title compound (110 mg, 0.50 mmol) as a yellow oil; C$_{14}$H$_{16}$O$_3$ (232.27).

$^1$H NMR (300 MHz, CDCl$_3$): δ=1.46 (t, J=7.0 Hz, 3H), 3.88 (s, 3H), 4.10 (q, J=7.0 Hz, 2H), 5.87 (dd, J=10.5 Hz, J=1.5 Hz, 1H; E-5-H), 5.87 (s, 1H; 1-H), 5.89 (s, 1H; 1-H), 6.34 (dd, J=17.4 Hz, J=1.6 Hz, 1H; Z-5-H), 6.73 (dd, J=17.3 Hz, J=10.5 Hz, 1H; 4-H), 6.84-6.93 (m, 3H) ppm.

E2. 2-(3,4-dimethoxy-phenyl)-1,4-pentadien-3-one

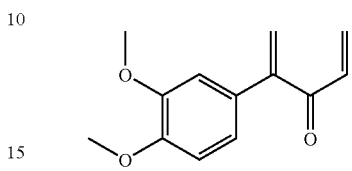

According to the General Procedure B, MnO$_2$ (1.81 g, 20.79 mmol) and 2-(3,4-dimethoxyphenyl)-1,4-pentadien-3-ol (220 mg, 0.99 mmol) are converted to give after workup and chromatography (SiO$_2$, PE/EE=2:1, R$_f$=0.40) the title compound (122 mg, 0.56 mmol, 56%) as a yellow oil; C$_{14}$H$_{16}$O$_3$ (218.25).

$^1$H NMR (300 MHz, CDCl$_3$): δ=3.88 (s, 3H; OCH$_3$), 3.90 (s, 3H; OCH$_3$), 5.88 (dd, J=10.5 Hz, J=1.6 Hz, 1H; E-5-H), 5.90 (s, 1H; 1-H), 5.92 (s, 1H; 1-H), 6.35 (dd, J=17.2 Hz, J=1.5 Hz, 1H; Z-5-H), 6.75 (dd, J=17.3 Hz, J=10.5 Hz, 1H; 4-H), 6.84-6.95 (m, 3H; Ph) ppm.

General Procedure C for the Preparation of 2-aryl-1,4-pentadien-3-ols [Compounds of Formula (10)]

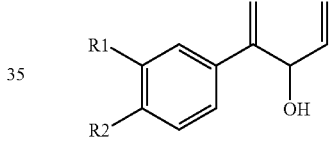

A bromostyrene derivative of formula (8) (1 equiv.) is added dropwise to a solution of t-BuLi (2.5 equiv.) in THF (2 l/mol) at −78° C., and the reaction mixture is stirred at −78° C. for 1.5 h. Then freshly distilled acrolein (3 equiv.) is added dropwise. After being stirred for a further 1.5 h at −78° C., the reaction mixture is allowed to warm up to RT and is washed with an aqueous solution of NH$_4$Cl (7 l/mol). The layers are separated, and the aqueous layer is extracted with CH$_2$Cl$_2$ (7 l/mol). The combined organic layers are washed with water (5 l/mol) and dried (MgSO$_4$). After removal of all volatile materials, the residue is chromatographed on SiO$_2$ to give the corresponding 2-aryl-1,4-pentadien-3-ol derivative.

F1. 2-(3-Ethoxy-4-methoxyphenyl)-1,4-pentadien-3-ol

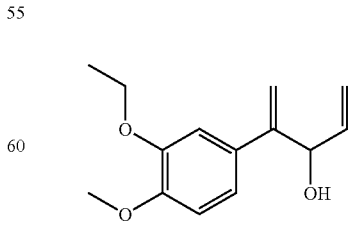

According to the General Procedure C, 1-bromo-1-(3-ethoxy-4-methoxyphenyl)ethene (1.40 g, 5.44 mmol), t-BuLi (8.00 ml, 13.60 mmol) and acrolein (914 mg, 16.32 mmol) are converted to give after workup and chromatography [SiO$_2$, PE/EE gradient from 5:1 to 2:1, R$_f$(PE/EE=2:1)=0.31] the title compound (1.10 g, 4.69 mmol) as a colorless oil;

$^1$H NMR (300 MHz, CDCl$_3$): δ=1.45 (t, J=7.0 Hz, 3H), 2.18 (d, br., J=3.5 Hz, 1H; OH), 3.87 (s, 3H), 4.06-4.15 (m, 2H), 5.08 (s, br., 1H; 3-H), 5.17 (dt, J=10.3 Hz, J=1.4 Hz, 1H; E-5-H), 5.32 (t, br., J=1.0 Hz, 1H; 1-H), 5.33 (s, br., 1H; 1-H), 5.34 (dt, J=17.2 Hz, J=1.4 Hz, 1H; Z-5-H), 5.96 (ddd, J=17.2 Hz, J=10.4 Hz, J=5.6 Hz, 1H; 4-H), 6.81-6.84 (m, 1H), 6.98-7.01 (m, 2H) ppm.

Anal. calcd. for C$_{14}$H$_{18}$O$_3$ (234.29): C 71.77, H 7.74; found: C 71.44, H 8.09. 2-(3-Ethoxy-4-methoxy-phenyl)-1,4-pentadien-3-ol shows sufficient long-term stability at +4° C.

F2. 2-(3,4-dimethoxyphenyl)-1,4-pentadien-3-ol

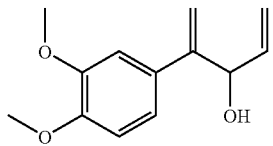

According to the General Procedure C, 1-bromo-1-(3,4-dimethoxyphenyl)ethene (1.00 g, 4.11 mmol), t-BuLi (6.05 ml, 10.28 mmol) and acrolein (691 mg, 12.33 mmol) are converted to give after workup and chromatography (SiO$_2$, PE/EE=2:1, R$_f$=0.25) the title compound (382 mg, 1.74 mmol, 42%) as a yellow oil; C$_{13}$H$_{16}$O$_3$ (220.26).

$^1$H NMR (500 MHz, CDCl$_3$): δ=1.95 (s, br., 1H; OH), 3.88 (s, 3H; OCH$_3$), 3.88 (s, 3H; OCH$_3$), 5.10 (d, J=5.5 Hz, 1H; 3-H), 5.19 (dt, J=10.3 Hz, J=1.2 Hz, 1H; E-5-H), 5.34 (s, 1H), 5.35 (s, 1H), 5.35 (dt, J=18.1 Hz, J=1.2 Hz, 1H), 5.97 (ddd, J=17.1 Hz, J=10.3 Hz, J=5.7 Hz, 1H; 4-H), 6.82-6.84 (m, 1H), 7.00-7.02 (m, 2H) ppm.

2-(3,4-dimethoxyphenyl)-1,4-pentadien-3-ol shows sufficient long-term stability at +4° C.

General Procedure D for the Preparation of Bromostyrenes [Compounds of Formula (11)]

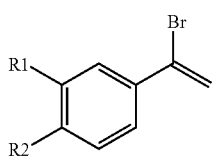

HBr (33% in acetic acid, 1 equiv.) is added dropwise to a phenylacetylene derivative of formula (9) (1 equiv.) under N$_2$ atmosphere. After being stirred for 15 min, water (5 l/mol) is added to the reaction mixture, and the layers are separated. The aqueous layer extracted with CH$_2$Cl$_2$ (10 l/mol). The combined organic layers are washed with a saturated aqueous solution of NaHCO$_3$ (4 l/mol), water (4 l/mol) and dried (MgSO$_4$). After removal of all volatile materials under vacuum, the residue is chromatographed on SiO$_2$ to give the corresponding bromostyrene derivative.

G1. 1-Bromo-1-(3-ethoxy-4-methoxyphenyl)ethene

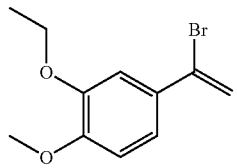

According to the General Procedure D, HBr (33% in acetic acid, 1.22 ml, 0.51 g, 6.25 mmol) and 3-Ethoxy-4-methoxyphenylacetylene (1.10 g, 6.25 mmol) are converted to give after workup and chromatography (SiO$_2$ PE/EE 5:1, R$_f$=0.35) the title compound (1.53 g, 5.83 mmol) as a brown oil; C$_{11}$H$_{13}$BrO$_2$ (257.13).

$^1$H NMR (300 MHz, CDCl$_3$): δ=1.48 (t, J=7.0 Hz, 3H; CH$_3$), 3.88 (s, 3H; OCH$_3$), 4.13 (q, J=7.0 Hz, 2H; OCH$_2$), 5.68 (d, J=2.0 Hz, 1H; CH$_2$), 6.01 (d, J=2.0 Hz, 1H; CH$_2$), 6.82 (d, J=8.4 Hz, 1H), 7.11 (d, J=2.2 Hz, 1H), 7.17 (dd, J=8.4 Hz, J=2.2 Hz, 1H) ppm.

1-Bromo-1-(3-ethoxy-4-methoxyphenyl)ethene shows no long-term stability at ambient temperature, but can be stored at −15° C. for a few days.

G2. 1-Bromo-1-(3,4-dimethoxyphenyl)ethene

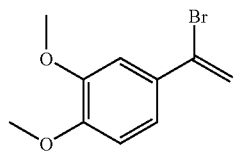

According to the General Procedure D, HBr (33% in acetic acid, 1.11 ml, 0.50 g, 6.17 mmol) and 3,4-di-methoxyphenylacetylene (1.00 g, 6.17 mmol) are converted to give after workup and chromatography (SiO$_2$, PE/EE 5:1, R$_f$=0.41) the title compound (1.30 g, 5.35 mmol, 87%) as a brown oil; C$_{10}$H$_{11}$BrO$_2$ (243.10).

$^1$H NMR (300 MHz, CDCl$_3$): δ=3.88 (s, 3H; OCH$_3$), 3.91 (s, 3H; OCH$_3$), 5.69 (d, J=1.7 Hz, 1H; CH$_2$), 6.02 (d, J=2.0 Hz, 1H; CH$_2$), 6.82 (d, J=8.4 Hz, 1H), 7.10 (d, J=2.2 Hz, 1H), 7.17 (dd, J=8.4 Hz, J=1.8 Hz, 1H) ppm.

1-Bromo-1-(3,4-dimethoxyphenyl)ethene shows no long-term stability at ambient temperature, but can be stored at −15° C. for a few days.

General Procedure E for the Preparation of Arylacetylenes [Compounds of Formula (12)]

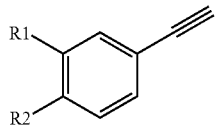

A 1-Aryl-2,2-dibromoethene derivative of formula (10) (1 equiv.) is dissolved in dry THF (6.5 dm$^3$ mol$^{-1}$) and the solution is cooled to −78° C. under N$_2$ atmosphere. n-BuLi (2.2 equiv.) is added to the stirred solution over a period of 0.5 h. Stirring is continued at −78° C. for 1 h, after which time the cooling bath is removed and the reaction mixture is stirred for 1.5 h at RT. The reaction is quenched with saturated aqueous NH$_4$Cl (12 l/mol) and extracted with CH$_2$Cl$_2$ (14 l/mol). The combined organic extracts are dried (MgSO$_4$), filtered, and evaporated. The residue is chromatographed on SiO$_2$ to give the corresponding arylacetylene derivative.

H1. 3-Ethoxy-4-methoxyphenylacetylene

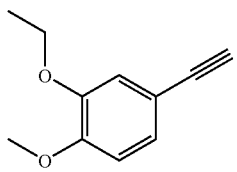

According to the General Procedure E, 2,2-dibromo-1-(3-ethoxy-4-methoxyphenyl)ethene (5.00 g, 14.88 mmol) and n-BuLi (20.46 ml, 32.74 mmol) are converted to give after workup and chromatography (SiO$_2$, PE/EE=5:1, R$_f$=0.31) the title compound (2.60 g, 14.76 mmol, 99%) as a colorless solid. M.p. 95-96° C.;

$^1$H NMR (500 MHz, CDCl$_3$): δ=1.46 (t, J=7.0 Hz, 3H), 2.99 (s, 1H), 3.87 (s, 3H), 4.09 (q, J=7.0 Hz, 2H), 6.80 (d, J=8.3 Hz, 1H), 6.99 (d, J=1.8 Hz, 1H), 7.09 (dd, J=8.3 Hz, J=1.8 Hz, 1H) ppm.

Anal. calcd. for C$_{11}$H$_{12}$O$_2$ (176.22): C 74.98, H 6.86; found: C 74.93, H 6.85.

H2. 3,4-Dimethoxyphenylacetylene

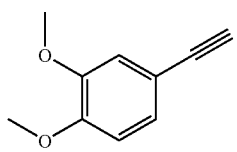

According to the General Procedure E, 2,2-dibromo-1-(3,4-dimethoxyphenyl)ethene (4.00 g, 12.40 mmol) and n-BuLi (17.11 ml, 27.28 mmol) are converted to give after workup and chromatography (SiO$_2$, PE/EE=1:1, R$_f$=0.51) the title compound (1.70 g, 10.48 mmol, 85%) as a colorless solid, m.p. 71-72° C.;

$^1$H NMR (500 MHz, CDCl$_3$): δ=3.01 (s, 1H; CH), 3.88 (s, 3H; OCH$_3$), 3.89 (s, 3H; OCH$_3$), 6.80 (d, J=8.3 Hz, 1H; CH), 6.99 (d, J=1.7 Hz, 1H; CH), 7.11 (dd, J=3.3 Hz, J=1.8 Hz, 1H; CH) ppm.

Anal. calcd. for C$_{10}$H$_{10}$O$_2$ (162.19): C 74.06, H 6.21; found: C 73.97, H 6.30.

General Procedure F for the Preparation of 1-aryl-2,2-dibromoethenes [Compounds of Formula (13)]

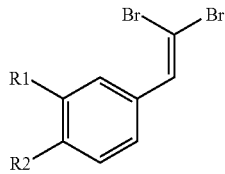

To a well stirred solution of carbon tetrabromide (1 equiv.) in dry CH$_2$Cl$_2$ (2.5 l/mol) at 0° C. is added tri-phenylphosphine (2 equiv.), and then a benzaldehyde derivative of formula 14 (1 equiv.). The resultant solution is stirred for 10-15 min, washed with water (2.5 l/mol), and dried (MgSO$_4$). After removal of all volatile materials under vacuum, the residue is chromatographed on SiO$_2$ to give the corresponding 1-aryl-2,2-dibromoethene derivative.

I1. 2,2-Dibromo-1-(3-ethoxy-4-methoxyphenyl)ethene

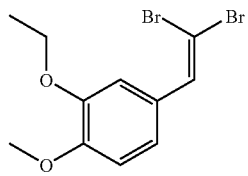

According to the General Procedure F, carbon tetrabromide (3.70 g, 11.10 mmol), triphenylphosphine (5.82 g, 22.20 mmol) and 3-Ethoxy-4-methoxybenzaldehyde (2.00 g, 11.10 mmol) are converted to give after workup and chromatography (SiO$_2$, CH$_2$Cl$_2$, R$_f$=0.55) the title compound (3.37 g, 10.03 mmol) as a pale yellow solid. M.p. 41-42° C.;

$^1$H NMR (500 MHz, CDCl$_3$): δ=1.46 (t, J=7.0 Hz, 3H; CH$_3$), 3.86 (s, 3H; OCH$_3$), 4.08 (q, J=7.0 Hz, 2H; OCH$_2$), 6.83 (d, J=8.4 Hz, 1H; CH), 7.10 (dd, J=8.4 Hz, J=2.0 Hz, 1H; CH), 7.18 (d, J=2.0 Hz, 1H; CH), 7.38 (s, 1H; CH) ppm.

Anal. calcd. for C$_{11}$H$_{12}$Br$_2$O$_2$(336.02): C 39.32, H 3.60; found: C 39.32, H 3.62.

I2. 2,2-Dibromo-1-(3,4-dimethoxyphenyl)ethene

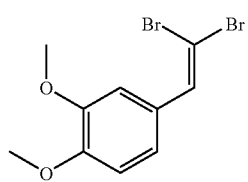

According to the General Procedure F, carbon tetrabromide (4.00 g, 12.05 mmol), triphenylphosphine (6.30 g, 24.10 mmol) and 3,4-dimethoxybenzaldehyde (2.00 g, 12.05 mmol) are converted to give after workup and chromatography (SiO$_2$, CH$_2$Cl$_2$, R$_f$=0.48) the title compound (3.76 g, 11.68 mmol, 97%) as a yellow oil.

$^1$H NMR (300 MHz, CDCl$_3$): δ=3.89 (s, 3H; OCH$_3$), 3.90 (s, 3H; OCH$_3$), 6.86 (d, J=8.4 Hz, 1H; CH), 7.10 (dd, J=8.4 Hz, J=2.3 Hz, 1H; CH), 7.19 (d, J=2.0 Hz, 1H; CH), 7.41 (s, 1H; CH) ppm.

Anal. calcd. for C$_{10}$H$_{10}$Br$_2$O$_2$(321.99): C 37.30, H 3.13; found: C 37.05, H 3.15.

Alternative Route to 3-Ethoxy-4-methoxyphenylacetylene:

H1. 3-Ethoxy-4-methoxyphenylacetylene

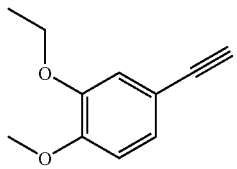

A solution of 3-Ethoxy-4-methoxyacetophenone (2.60 g, 13.4 mmol) in THF (7 ml) is slowly added to LDA (7.05 ml, 1.51 g, 14.07 mmol) in THF (10 ml) under N$_2$ atmosphere at −78° C., and the reaction mixture is stirred at −78° C. for 1 h. Then diethyl chlorophosphate (2.51 g, 14.07 mmol) is added, and the reaction mixture is warmed up to RT (3 h). After being cooled again to −78 cc, LDA (15.1 ml, 3.23 g, 30.15 mmol) is added dropwise over 30 min, and the reaction mixture is warmed up to RT (3 h). At 0° C. water is added (10 ml), and the reaction mixture is stirred for 20 min at 0° C. The layers are separated, and the aqueous layer is extracted with CH$_2$Cl$_2$ (3×50 ml). The combined extracts are washed with 1 N HCl (40 ml), washed with water (3×100 ml) and dried (MgSO$_4$). The solvent is removed under vacuum, and the residue is chromatographed on SiO$_2$ (PE/EE=5:1, R$_f$=0.31) to give the title compound as a colorless solid (1.33 g, 7.60 mmol, 56%). M.p. 95-96° C.

$^1$H NMR (500 MHz, CDCl$_3$): δ=1.46 (t, J=7.0 Hz, 3H), 2.99 (s, 1H), 3.87 (s, 3H), 4.09 (q, J=7.0 Hz, 2H), 6.80 (d, J=8.3 Hz, 1H), 6.99 (d, J=1.8 Hz, 1H), 7.09 (dd, J=8.3 Hz, J=1.8 Hz, 1H) ppm.

Anal. calcd. for C$_{11}$H$_{12}$O$_2$ (176.22): C 74.98, H 6.86; found: C 74.93, H 6.85.

K. 3-Ethoxy-4-methoxyacetophenone

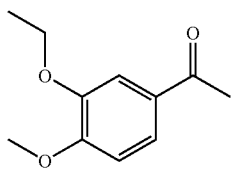

A suspension of 3-Hydroxy-4-methoxyacetophenone (4.00 g, 24.1 mmol) and K$_2$CO$_3$ (4.77 g, 48.1 mmol) in DMF (20 ml) is heated at 100° C. for 30 min and then cooled to RT. Ethyl bromide (5.25 g, 48.14 mmol) is slowly added dropwise, and the reaction mixture is heated at 100° C. for 6 h. After removal of the sol-vent, the residue is dissolved in water (40 ml) and extracted with CH$_2$Cl$_2$ (3×50 ml). The combined ex-tracts are dried (MgSO$_4$) and concentrated. The crude product is recrystallized from 2-propanol (25 ml) to give the title compound as fine needles (3.97 g, 20.44 mmol). M.p. 63-64° C.

$^1$H NMR (500 MHz, CDCl$_3$): δ=1.48 (t, J=7.0 Hz, 3H; CH$_3$), 2.56 (s, 3H; CH$_3$), 3.94 (s, 3H; CH$_3$), 4.16 (q, J=7.0 Hz, 2H; OCH$_2$), 6.88 (d, J=8.4 Hz, 1H; CH), 7.52 (d, J=1.9 Hz, 1H; CH), 7.57 (dd, J=8.4 Hz, J=1.9 Hz, 1H; CH) ppm.

Anal. calcd. for C$_{11}$H$_{14}$O$_3$ (194.23): C 68.02, H 7.26; found: C 67.90, H 7.36.

L. 3-Hydroxy-4-methoxyacetophenone

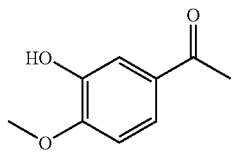

A solution of 3,4-dimethoxy-acetophenone (15 g, 83 mmol) in conc. H$_2$SO$_4$ (75 ml) is stirred at 65° C. for 46 h. After being cooled to RT, the reaction mixture is poured on ice (300 g) and stirred for 1 h. The precipitate is filtered off, washed with water, and redissolved in NaOH (1 mol/l, 190 ml, 0.19 mol). The mixture is extracted with CH$_2$Cl$_2$ (80 ml). The aqueous NaOH layer is acidified with conc. HCl (30 ml), stirred for 1.5 h (ice-cooling) and filtered off to give precipitated 3-Hydroxy-4-methoxyacetophenone as a light brown solid (8.291 g, 49.89 mmol). M.p. 72-74° C.;

$^1$H NMR (500 MHz, CDCl$_3$): δ=2.55 (s, 3H; CH$_3$), 3.93 (s, 3H; OCH$_3$), 5.94 (s, 1H; OH), 6.90-6.92 (m, 1H), 7.56-7.57 (m, 2H) ppm.

Anal. calcd. for C$_9$H$_{10}$O$_3$ (166.18): C 65.05, H 6.07; found: C 64.70, H 6.08.

The numbering and the names of the compounds according to the invention throughout the description and the claims have been generated by the program Autonom 2000 of MDL Information systems GmbH. In the following Table is presented a concordance list of the numbering and names generated by Autonom 2000 and the numbering and the names generated by ACD IUPAC Names, ScienceServe Elsevier MDL (IUPAC conform):

| Numbering and names generated by Autonom 2000 | Numbering and names generated by ACD IUPAC Names (IUPAC conform) |
|---|---|
| Numbering: 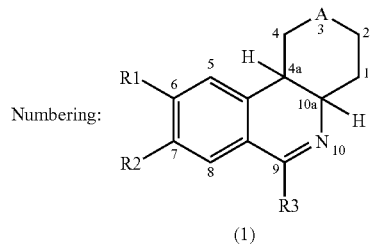 (1) | Numbering: 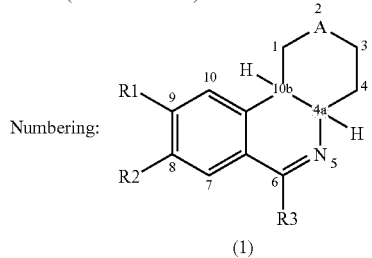 (1) |

End Products 1-5

| | |
|---|---|
| 1. 4-((4aR,10aR)-6-Ethoxy-7-methoxy-1,4,4a,10a-tetrahydro-2H-3-thia-10-aza-phenanthren-9-yl)-N,N-diisopropyl-benzamide | 4-[(4aR,10bR)-9-Ethoxy-8-methoxy-3,4,4a,10b-tetrahydro-1H-thiopyrano[4,3-c]isoquinolino-6-yl]-N,N-diisopropylamide |
| 2. 4-((4aR,10aR)-6-Ethoxy-7-methoxy-3-oxo-1,2,3,4,4a,10a-hexahydro-3$l^4$-thia-10-aza-phenanthren-9-yl)-N,N-diisopropyl-benzamide (Diastereomer A) | 4-[(4aR,10bR)-9-Ethoxy-8-methoxy-2-oxido-3,4,4a,10b-tetrahydro-1H-thiopyrano[4,3-]-isoquinolino-6-yl]-N,N-diisopropylbenzamide (Diastereomer A) |
| 3. 4-((4aR,10aR)-6-Ethoxy-7-methoxy-3-oxo-1,2,3,4,4a,10a-hexahydro-3$l^4$-thia-10-aza-phenanthren-9-yl)-N,N-diisopropyl-benzamide (Diastereomer B) | 4-[(4aR,10bR)-9-Ethoxy-8-methoxy-2-oxido-3,4,4a,10b-tetrahydro-1H-thiopyrano[4,3-c]-isoquinolino-6-yl]-N,N-diisopropylbenzamide (Diastereomer B) |
| 4. 4-((4aR,10aR)-6-Ethoxy-7-methoxy-3,3-dioxo-1,2,3,4,4a,10a-hexahydro-3$l^6$-thia-10-aza-phenanthren-9-yl)-N,N-diisopropyl-benzamide | 4-[(4aR,10bR)-9-Ethoxy-8-methoxy-2,2-dioxido-3,4,4a,10b-tetrahydro-1H-thiopyrano[4,3-c]-isoquinolino-6-yl]-N,N-diisopropylbenzamide |
| 5. 4-((4aR,10aR)-6-Ethoxy-7-methoxy-3,3-dioxo-10-oxy-1,2,3,4,4a,10a-hexahydro-3$l^6$-thia-10-aza-phenanthren-9-yl)-N,N-diisopropyl-benzamide | 4-[(4aR,10bR)-9-Ethoxy-8-methoxy-2,2,5-trioxido-3,4,4a,10b-tetrahydro-1H-thiopyrano[4,3-c]-isoquinolino-6-yl]-N,N-diisopropylbenzamide |

Starting Products and Intermediates A1-D2

| | |
|---|---|
| A1. N-[(3R,4R)-3-(3-ethoxy-4-methoxy-phenyl)-1,1-dioxo-hexahydro-1$l^6$-thiopyran-4-yl]-N',N'-diisopropyl-terephthalamide | N-[3R,4R)-3-(3-ethoxy-4-methoxyphenyl)-1,1-dioxidotetrahydro-2H-thiopyran-4-yl]-N,N-diisopropylterephthalamide |
| A2. N-[(3R,4R)-3-Ethoxy-4-methoxy-phenyl)-tetrahydro-thiopyran-4-yl]-N',N'-diisopropyl-terephthalamide | N-[(3R,4R)-3-(3-ethoxy-4-methoxyphenyl)tetrahydro-2H-thiopyran-4-yl]-N,N-diisopropylterephthalamide |
| B1. (3R,4R)-3-(3-Ethoxy-4-methoxy-phenyl)-1,1-dioxo-1$l^6$-hexahydro-thiopyran-4-ylamine | (3R,4R)-3-(3-Ethoxy-4-methoxyphenyl)tetrahydro-2H-thiopyran-4-amine 1,1-dioxide |
| B2. (3R,4R)-3-(3-Ethoxy-4-methoxy-phenyl)-1,1-dioxo-1$l^6$-hexahydro-thiopyran-4-ylamine hydrochloride | (3R,4R)-3-(3-Ethoxy-4-methoxyphenyl)tetrahydro-2H-thiopyran-4-amine hydrochloride |
| B3. [(3R,4R)-3-(3-Ethoxy-4-methoxy-phenyl)-tetrahydro-thiopyran-4-yl]-((R)-1-phenyl-ethyl)-amine hydrochloride | (3R,4R)-3-(3-Ethoxy-4-methoxyphenyl)-N-[(1R)-1-phenylethyl]tetrahydro-2H-thiopyran-4-amine hydrochloride |
| C. 3-(3-Ethoxy-4-methoxy-phenyl)-1,1-dioxo-tetrahydro-1$l^6$-thiopyran-4-one | 3-(3-Ethoxy-4-methoxyphenyl)tetrahydro-2H-thiopyran-4-one 1,1-dioxide |
| D1. 3-(3-Ethoxy-4-methoxy-phenyl)-tetrahydro-thiopyran-4-one | 3-(3-Ethoxy-4-methoxyphenyl)tetrahydro-2H-thiopyran-4-one |
| D2. 3-(3,4-Dimethoxyphenyl)tetrahydrothiopyran-4-one | 3-(3,4-Dimethoxyphenyl)tetrahydro-2H-thiopyran-4-one |

Commercial Utility Beachte PDE3/4 Version gegen PDE4 Version ausgetauscht

The compounds according to the invention have useful pharmacological properties which make them industrially utilizable. As selective cyclic nucleotide phosphodiesterase (PDE) inhibitors (specifically of type 4), they are suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways (asthma prophylaxis), of the skin, of the intestine, of the eyes, of the CNS and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. In this context, the compounds according to the invention are distinguished by a low toxicity, a good enteral absorption (high bioavailability), a large therapeutic breadth and the absence of significant side effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of varying origin (bronchitis, allergic bronchitis, bronchial asthma, emphysema, COPD); dermatoses (especially of proliferative, inflammatory and allergic type) such as psoriasis (vulgaris), toxic and allergic contact eczema, atopic eczema, seborrhoeic eczema, Lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on an excessive release of TNF and leukotrienes, for example disorders of the arthritis type (rheumatoid arthritis, rheumatoid spondylitis, osteoarthritis and other arthritic conditions), disorders of the immune system (AIDS, multiple sclerosis), graft versus host reaction, allograft rejections, types of shock (septic shock, endotoxin shock, gram-negative sepsis, toxic shock syndrome and ARDS (adult respiratory distress syndrome)) and also generalized inflammations in the gastrointestinal region (Crohn's disease and ulcerative colitis); disorders which are based on allergic and/or chronic, immunological false reactions in the region of the upper air-ways (pharynx, nose) and the adjacent regions (paranasal sinuses, eyes), such as allergic rhinitis/sinusitis, chronic rhinitis/sinusitis, allergic conjunctivitis and also nasal polyps; but also disorders of the heart which can be treated by PDE inhibitors, such as cardiac insufficiency, or disorders which can be treated on account of the tissue-relaxant action of the PDE inhibitors, such as, for example, erectile dysfunction or colics of the kidneys and of the ureters in connection with kidney stones. In addition, the compounds of the invention are useful in the treatment of diabetes insipidus, diabetes mellitus type I and type II, leukaemia, osteoporosis and conditions associated with cerebral metabolic inhibition, such as cerebral senility, senile dementia (Alzheimer's disease), memory impairment associated with Parkinson's disease or multiinfarct dementia; and also illnesses of the central nervous system, such as depressions or arteriosclerotic dementia.

The invention further relates to the compounds, pharmaceutically acceptable hydrates, solvates, salts or N-oxides according to the invention for use in the treatment and/or prophylaxis of diseases, especially the above exemplified diseases.

The invention furthermore relates to pharmaceutical compositions, specifically for the treatment and/or prophylaxis of the above-exemplified diseases, which comprise one or more compounds, pharmaceutically acceptable hydrates, solvates, salts or N-oxides according to the invention together with one or more pharmaceutically acceptable auxiliaries and/or excipients.

The invention also relates to the use of the compounds, pharmaceutically acceptable hydrates, solvates, salts or N-oxides according to the invention in the manufacture of a pharmaceutical composition for the treatment and/or prophylaxis of a disease, in which PDE4 (PDE3/4) inhibition is beneficial, particularly a pharmaceutical composition for the treatment and/or prophylaxis of one or more of the above exemplified diseases.

The invention further relates to a method for the treatment and/or prophylaxis of one or more disease(s), in which PDE4 (or PDE3/4) inhibition is beneficial, in a mammal, including humans, who are suffering from said disease(s) or are susceptible to said disease(s), in particular wherein said disease(s) is one or more of the above exemplified disease(s). The method is characterized in that a therapeutically or prophylactically effective amount of one or more compounds, hydrates, solvates, salts or N-oxides according to the invention is administered to the mammal in need of such treatment and/or prophylaxis.

The pharmaceutical compositions can contain one or more of the compounds, pharmacologically accept-able hydrates, solvates, salts or N-oxides according to the invention (hereinafter referred to as "the active compound") in a total amount of from 0.1 to 99.9 wt %, preferably 5 to 95 wt %, more preferably 20 to 80 wt %.

As pharmaceutically acceptable auxiliaries and excipients, any auxiliaries and excipients known to be suitable for preparing pharmaceutical compositions can be used. Examples thereof include, but are not limited to, solvents, dispersants, emulsifiers, solubilizers, gel formers, ointment bases, antioxidants, preservatives, stabilizers, carriers, fillers, binders, thickeners, complexing agents, disintegrating agents, buffers, permeation promoters, polymers, lubricants, coating agents, propellants, tonicity adjusting agents, surfactants, colorants, flavorings, sweeteners and dyes. In particular, auxiliaries and excipients of a type appropriate to the desired formulation and the desired mode of administration are used.

The pharmaceutical compositions can be formulated, for example, into tablets, coated tablets (dragees), pills, cachets, capsules (caplets), granules, powders, suppositories, solutions (e.g. sterile solutions), emulsions, suspensions, ointments, creams, lotions, pastes, oils, gels, sprays and patches (e.g. trans-dermal therapeutic systems). Additionally, the pharmaceutical compositions can be prepared as e.g. liposome delivery systems and systems in which the active compound is coupled to polymers (e.g. soluble or biodegradable polymers).

The pharmaceutical compositions comprising one or more of the active compounds and one or more auxiliaries and/or excipients can be manufactured in a manner known to a person skilled in the art, e.g. by dissolving, mixing, granulating, dragee-making, levigating, emulsifying, encapsulating, entrapping or lyophilizing processes.

The selected formulation depends inter alia on the route of administering the pharmaceutical composition. The pharmaceutical compositions of the present invention can be administered by any suitable route, for example by the oral, sublingual, buccal, intravenous, intramuscular, subcutaneous, intracutaneous, topical, transdermal, intranasal, intraocular, intaperitoneal, intrasternal, intracoronary, transurethral, rectal or vaginal administration, by inhalation or by insufflation. Oral administration is preferred.

Specifically, tablets, coated tablets (dragees), pills, cachets, capsules (caplets), granules, solutions, emulsions and suspensions are e.g. suitable for oral administration. In particular, said formulations can be adapted so as to represent, for example, an enteric form, an immediate release form, a delayed release form or a sustained release form. Said forms can be obtained, for example, by coating tablets, by dividing tablets into several compartments separated by layers disintegrating under different conditions (e.g. pH conditions) or by coupling the active compound to a biodegradable polymer.

Administration by inhalation is preferably made by using an aerosol. The aerosol is a liquid-gaseous dispersion, a solid-gaseous dispersion or a mixed liquid/solid-gaseous dispersion.

The aerosol may be generated by means of aerosol-producing devices such as dry powder inhalers (DPIs), pressurized metered dose inhalers (PMDIs) and nebulizers. Depending on the kind of active compound to be administered, the aerosol-producing device can contain the active compound in form of a powder, a solution or a dispersion. The powder may contain, for example, one or more of the following auxiliaries: carriers, stabilizers and fillers. The solution may contain in addition to the solvent, for example, one or more of the following auxiliaries: propellants, solubilizers (co-solvents), surfactants, stabilizers, buffers, tonicity adjusting agents, preservatives and flavorings. The dispersion may contain in addition to the dispersant, for example, the following auxiliaries: one or more propellants, surfactants, stabilizers, buffers, preservatives and flavorings. Examples of carriers include, but are not limited to, saccharides, e.g. lactose and glucose. Examples of propellants include, but are not limited to, fluoro-hydrocarbons, e.g. 1,1,1,2-tetrafluoroethane and 1,1,1,2,3,3,3-heptafluoropropane.

The particle size of the aerosol particles (solid, liquid or solid/liquid particles) is preferably less than 100 µm, more preferably it is in the range of from 0.5 to 10 µm, in particular in the range of from 2 to 6 µm (D50 value, measured by laser diffraction).

Specific aerosol-producing devices which may be used for inhaled administration include, but are not limited to, Cyclohaler®, Diskhaler®, Rotadisk®, Turbohaler®, Autohaler®, Turbohaler®, Novolizer®, Easyhaler®, Aerolizer®, Jethaler®, Diskus®, Ultrahaler® and Mystic® inhalers. The aerosol-producing devices may be combined with spacers or expanders, e.g. Aerochamber®, Nebulator®, Volumatic® and Rondo®, for improving inhalation efficiency.

In case of topical administration suitable pharmaceutical formulations are, for example, ointments, creams, lotions, pastes, gels, powders, solutions, emulsions, suspensions, oils, sprays and patches (e.g. transdermal therapeutic systems).

For parenteral modes of administration such as, for example, intravenous, intramuscular, subcutaneous, intracutaneous, intaperitoneal and intrasternal administration, preferably solutions (e.g. sterile solutions, isotonic solutions) are used. They are preferably administered by injection or infusion techniques.

In case of intranasal administration, for example, sprays and solutions to be applied in drop form are preferred formulations.

For intraocular administration, solutions to be applied in drop form, gels and ointments are exemplified formulations.

Generally, the pharmaceutical compositions according to the invention can be administered such that the dose of the active compound is in the range customary for PDE inhibitors. The dose for administration by inhalation is customarily between 0.1 and 3 mg per day. The customary dose in the case of systemic therapy (p.o. or i.v.) is between 0.01 and 10 mg per kilogram per day, preferably between 0.03 and 3 mg per kilogram per day. In this respect, it is to be noted that the dose is dependent, for example, on the specific compound used, the species treated, age, body weight, general health, sex and diet of the subject treated, mode and time of administration, rate of excretion, severity of the disease to be treated and drug combination. The pharmaceutical composition can be administered in a single dose per day or in multiple subdoses, for example 2 to 4 doses per day.

Biological Investigations beachte nur PDE4 Version

The second messenger cyclic AMP (cAMP) is well-known for inhibiting inflammatory and immunocompetent cells. The PDE4 isoenzyme is broadly expressed in cells involved in the initiation and propagation of inflammatory diseases (H Tenor and C Schudt, in "Phosphodiesterase Inhibitors", 21-40, "The Hand-book of Immunopharmacology", Academic Press, 1996), and its inhibition leads to an increase of the intracellular cAMP concentration and thus to the inhibition of cellular activation (J E Souness et al., Immunopharmacology 47: 127-162, 2000).

The antiinflammatory potential of PDE4 inhibitors in vivo in various animal models has been described (M M Teixeira, TiPS 18: 164-170, 1997). For the investigation of PDE4 inhibition on the cellular level (in vitro), a large variety of proinflammatory responses can be measured. Examples are the superoxide production of neutrophilic (C Schudt et al., Arch Pharmacol 344: 682-690, 1991) or eosinophilic (A Hatzelmann et al., Brit J Pharmacol 114: 821-831, 1995) granulocytes, which can be measured as luminol-enhanced chemiluminescence, or the synthesis of tumor necrosis factor-α in monocytes, macrophages or dendritic cells (Gantner et al., Brit J Pharmacol 121: 221-231, 1997, and Pulmonary Pharmacol Therapy 12: 377-386, 1999). In addition, the immunomodulatory potential of PDE4 inhibitors is evident from the inhibition of T-cell responses like cytokine synthesis or proliferation (D M Essayan, Biochem Pharmacol 57: 965-973, 1999). Substances which inhibit the secretion of the aforementioned proinflammatory mediators are those which inhibit PDE4. PDE4 inhibition by the compounds according to the invention is thus a central indicator for the suppression of inflammatory processes.

Method for Measuring Inhibition of PDE3 and PDE4 Activities beachte nur PDE4 Version The PDE4B2 (GB no. M97515) was a gift of Prof. M. Conti (Stanford University, USA). It was amplified from the original plasmid (pCMV5) via PCR with primers Rb9 (5'-GCCAGCGTGCAAATAATGAAGG-3') and Rb10 (5'-AGAGGGGGATTATGTATCCAC-3') and cloned into the pCR-Bac vector (Invitrogen, Groningen, NL).

The recombinant baculovirus was prepared by means of homologous recombination in SF9 insect cells. The expression plasmids were cotransfected with Bac-N-Blue (Invitrogen, Groningen, NL) or Baculo-Gold DNA (Pharmingen, Hamburg) using a standard protocol (Pharmingen, Hamburg). Wt virus-free recombinant virus supernatants were selected using plaque assay methods. After that, high-titre virus supernatants were prepared by amplifying 3 times. PDE4B2 was expressed in SF21 cells by infecting $2 \times 10^6$ cells/ml with an MOI (multiplicity of infection) between 1 and 10 in serum-free SF900 medium (Life Technologies, Paisley, UK). The cells were cultured at 28° C. for 48-72 hours, after which they were pelleted for 5-10 min at 1000 g and 4° C.

The SF21 insect cells were resuspended, at a concentration of approx. $10^7$ cells/ml, in ice-cold (4%) homogenization buffer (20 mM Tris, pH 8.2, containing the following additions: 140 mM NaCl, 3.8 mM KCl, 1 mM EGTA, 1 mM $MgCl_2$, 10 mM-mercaptoethanol, 2 mM benzamidine, 0.4 mM Pefablock, 10 µM leupeptin, 10 µM pepstatin A, 5 µM trypsin inhibitor) and disrupted by ultrasonication. The homogenate was then centrifuged for 10 min at 1000×g and the supernatant was stored at −80° C. until sub-sequent use (see below). The protein content was determined by the Bradford method (BioRad, Munich) using BSA as the standard.

PDE4B2 activity was inhibited by the said compounds in a modified SPA (scintillation proximity assay) test, supplied by Amersham Biosciences (see procedural instructions "phosphodiesterase [3H]cAMP SPA enzyme assay, code TRKO 7090"), carried out in 96-well microtitre plates (MTP's). The test volume is 100 µl and contains 20 mM Tris buffer (pH 7.4), 0.1 mg of BSA (bovine serum albumin)/ml, 5 mM $Mg^{2+}$, 0.5 µM cAMP (including about 50,000 cpm of [3H]cAMP), 1 µl of the respective substance dilution in DMSO and sufficient recombinant PDE (1000×g supernatant, see above) to ensure that 10-20% of the cAMP is converted under the said experimental conditions. The final concentration of DMSO in the assays (1% v/v) does not substantially affect the activity of the PDEs investigated. After a preincubation of 5 min at 37° C., the reaction is started by adding the substrate (cAMP) and the assays are incubated for a further 15 min; after that, they are stopped by adding SPA beads (50 µl). In accordance with the manufacturer's instructions, the SPA beads had previously been resuspended in water, but were then diluted 1:3 (v/v) in water; the diluted solution also contains 3 mM IBMX to ensure a complete PDE activity stop. After the beads have been sedimented (>30 min), the MTP's are analyzed in commercially available luminescence detection devices. The corresponding $IC_{50}$ values of the compounds for the inhibition of PDE activities are determined from the concentration-effect curves by means of non-linear regression.

The inhibitory values determined for the compounds according to the invention follow from the following Table 1, in which the numbers of the compounds correspond to the numbers of the examples.

TABLE 1

Inhibition of PDE4 acitivity [measured as $-\log IC_{50}$ (mol/l)]

| Compound | PDE4 Inhibition |
|---|---|
| 1 | 9.14 |
| 2 | 6.84 |
| 3 | 8.48 |
| 5 | 7.7 |

The invention claimed is:

1. A process for the preparation of a compound of formula 8

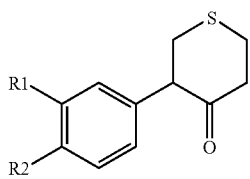
(8)

in which
R1 is 1-4C-alkoxy, 3-7C-cycloalkoxy, 3-7C-cycloalkyl-methoxy or 1-4C-alkoxy which is completely or predominantly substituted by fluorine,
R2 is 1-4C-alkoxy, 3-7C-cycloalkoxy, 3-7C-cycloalkyl-methoxy or 1-4C-alkoxy which is completely or predominantly substituted by fluorine,
or in which
R1 and R2 together are a 1-2C-alkylenedioxy group, comprising:
(a) reacting a compound of formula 12

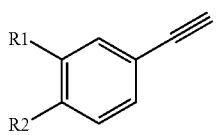
(12)

with concentrated hydrobromic acid under strictly anhydrous conditions,
(b) subjecting the resulting 1-bromo-1-(3,4-dialkoxyphenyl)ethane derivative of formula 11

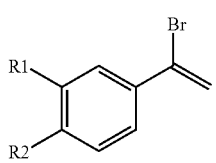
(11)

to a bromo-lithium exchange reaction and then converting with acrolein to yield a 2-(3,4-dialkoxyphenyl)-1,4-pentadien-3-ol derivative of formula 10

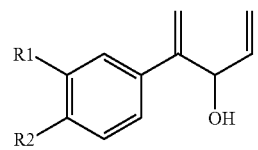
(10)

(c) oxidizing the 2-(3,4-dialkoxyphenyl)-1,4-pentadien-3-ol derivative of formula 10 to the corresponding 2-(3,4-dialkoxyphenyl)-1,4-pentadien-3-one derivative of formula 9

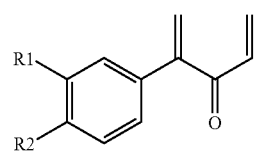
(9)

(d) and converting the 2-(3,4-dialkoxyphenyl)-1,4-pentadien-3-one derivative of formula 9 to a 3-(3,4-dialkoxyphenyl)-tetrahydro-thiopyran-4-one derivative of formula 8 via a double Michael addition with $Na_2S$ or NaHS.

2. A compound of formula 8

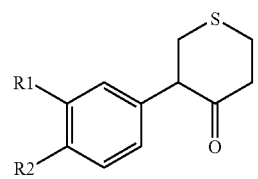
(8)

in which
R1 is 1-4C-alkoxy, 3-7C-cycloalkoxy, 3-7C-cycloalkyl-methoxy or 1-4C-alkoxy which is completely or predominantly substituted by fluorine and
R2 is 1-4C-alkoxy, 3-7C-cycloalkoxy, 3-7C-cycloalkyl-methoxy or 1-4C-alkoxy which is completely or predominantly substituted by fluorine,
or in which
R1 and R2 together are a 1-2C-alkylenedioxy group.

3. A compound of formula 7

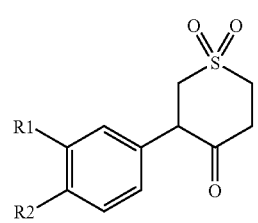
(7)

in which

R1 is 1-4C-alkoxy, 3-7C-cycloalkoxy, 3-7C-cycloalkyl-methoxy or 1-4C-alkoxy which is completely or predominantly substituted by fluorine and R2 is 1-4C-alkoxy, 3-7C-cycloalkoxy, 3-7C-cycloalkyl-methoxy or 1-4C-alkoxy which is completely or predominantly substituted by fluorine, or in which R1 and R2 together are a 1-2C-alkylenedioxy group.

4. A compound of formula 8 according to claim 2 in which

R1 is methoxy or ethoxy and

R2 is methoxy or ethoxy.

5. A compound of formula 8 according to claim 2 selected from

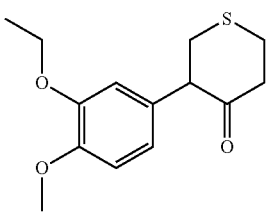

and

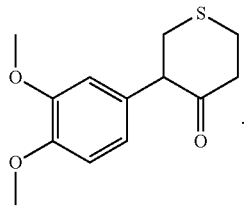

6. A compound of formula 7 according to claim 3, in which

R1 is methoxy or ethoxy and

R2 is methoxy or ethoxy.

7. A compound of formula 7 according to claim 3 which is

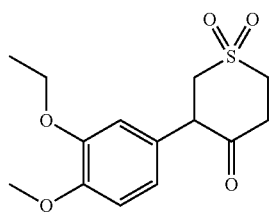

* * * * *